United States Patent
Maruo

(10) Patent No.: US 7,265,369 B2
(45) Date of Patent: Sep. 4, 2007

(54) METHOD AND SYSTEM FOR DETECTING CHEMICAL SUBSTANCE

(75) Inventor: Kazuyuki Maruo, Tokyo (JP)

(73) Assignee: Advantest Corp., Tokyo (JP)

( * ) Notice: Subject to any disclaimer, the term of this patent is extended or adjusted under 35 U.S.C. 154(b) by 0 days.

(21) Appl. No.: 10/250,559

(22) PCT Filed: Jan. 17, 2002

(86) PCT No.: PCT/JP02/00267

§ 371 (c)(1),
(2), (4) Date: Dec. 29, 2003

(87) PCT Pub. No.: WO02/057754

PCT Pub. Date: Jul. 25, 2002

(65) Prior Publication Data

US 2004/0108472 A1    Jun. 10, 2004

(30) Foreign Application Priority Data

Jan. 19, 2001 (JP) ............................. 2001-011604
Mar. 21, 2001 (JP) ............................. 2001-068863

(51) Int. Cl.
*G01J 1/00* (2006.01)
*G01J 5/02* (2006.01)
(52) U.S. Cl. ............................. 250/504 R; 250/339.11
(58) Field of Classification Search ............ 250/504 R, 250/341.8, 339.11, 339.06, 339.01, 338.1, 250/370.06, 503.1; 356/300, 238.3, 237.3

See application file for complete search history.

(56) References Cited

U.S. PATENT DOCUMENTS

| | | | | | |
|---|---|---|---|---|---|
| 5,332,901 | A | * | 7/1994 | Eckles et al. | 250/345 |
| 5,747,808 | A | * | 5/1998 | Wong | 250/343 |
| 6,052,191 | A | * | 4/2000 | Brayden et al. | 356/630 |
| 6,207,460 | B1 | * | 3/2001 | Kishkovich et al. | 436/106 |
| 6,217,695 | B1 | * | 4/2001 | Goldberg et al. | 156/244.17 |
| 6,392,745 | B1 | * | 5/2002 | Mavliev et al. | 356/37 |
| 6,476,393 | B1 | * | 11/2002 | Yoshida et al. | 250/341.8 |
| 6,657,196 | B2 | * | 12/2003 | Endo et al. | 250/339.11 |
| 6,660,528 | B1 | * | 12/2003 | Chen et al. | 436/171 |
| 2001/0011640 | A1 | * | 8/2001 | Suzuki et al. | 205/765 |
| 2003/0052281 | A1 | * | 3/2003 | Rader et al. | 250/461.1 |
| 2003/0183503 | A1 | * | 10/2003 | Fujii | 204/157.3 |
| 2004/0056196 | A1 | * | 3/2004 | Yoshida et al. | 250/336.1 |
| 2004/0113097 | A1 | * | 6/2004 | Marchman et al. | 250/492.2 |
| 2005/0082000 | A1 | * | 4/2005 | Moriya et al. | 156/345.28 |

(Continued)

FOREIGN PATENT DOCUMENTS

JP    6-8243    3/1994

(Continued)

*Primary Examiner*—David Porta
*Assistant Examiner*—Faye Boosalis
(74) *Attorney, Agent, or Firm*—Muramatsu & Associates

(57) ABSTRACT

A chemical detecting apparatus includes a substrate 10 for chemicals in gas-to-be-monitored to be adsorbed to, a substrate adsorption rate improving means 12 which enhances the adsorption of the chemical in the gas-to-be-monitored to the substrate, an infrared light source 20 which applies an infrared light to the substrate 10 with the chemical adsorbed to, and an infrared light detector 22 which detects the infrared light which has made multiple reflections in the substrate 10 and exited the substrate. Thus, chemicals present in environments can be detected at high speed and with high sensitivity.

24 Claims, 14 Drawing Sheets

U.S. PATENT DOCUMENTS

2005/0224458 A1 * 10/2005 Gaudet et al. .............. 216/67

FOREIGN PATENT DOCUMENTS

| JP | 7-174676    | 7/1995  |
|----|-------------|---------|
| JP | 9-145611    | 6/1997  |
| JP | 11-176878   | 7/1999  |
| JP | 11-326193   | 11/1999 |
| JP | 2000-55815  | 2/2000  |
| JP | 2000-70704  | 3/2000  |
| JP | 2000-91295  | 3/2000  |
| JP | 2001-165769 | 6/2001  |
| JP | 2001-194297 | 7/2001  |
| JP | 2001-194320 | 7/2001  |
| JP | 2001-305072 | 10/2001 |
| JP | 2001-311697 | 11/2001 |
| JP | 2001-343323 | 12/2001 |
| JP | 2001-343324 | 12/2001 |

* cited by examiner

METHOD AND SYSTEM FOR DETECTING CHEMICAL SUBSTANCE

TECHNICAL FIELD

The present invention relates to a chemical detecting method and apparatus which can analyze chemicals present in an environment with high sensitivity and at high speed.

BACKGROUND ART

It is increasingly important to environments surrounding our daily life to monitor chemicals present in the environments.

For example, recently environmental pollution caused by traces of chemicals, such as dioxine, etc., discharged from refuse incineration facilities is noted.

Instances that chemicals called VOC (Volatile Organic Compound) contained in construction materials of new houses, mansions evaporate in the rooms to damage the dwellers' health are reported, which is a serious problem called a sick house syndrome.

It is urgently necessary to monitor with high sensitivity and accuracy the traces of chemicals present in the environments as described above to thereby identify sources of the chemicals, and control discharge amounts of the chemicals to the environments. To this end, it is urgently necessary to develop environmental sensors which can detect the chemicals in real time with high sensitivity and identify chemicals present in environments.

As conventional methods for measuring chemicals in atmospheres, heating leaving GC-MS (Gas Chromatography-Mass Spectroscopy) and FTIR (Fourier Transform Infrared Spectroscopy), etc. are known.

In the heating leaving GC-MS, first a gas-to-be-monitored is adsorbed on a porous material, such as TENAX or others. Then, the porous material is heated to leave chemicals adsorbed on the porous material, and components of the chemicals are identified and determined by a mass spectroscope. Thus, component separation and structural analysis of traces of chemicals can be made in a series of measurements.

In the FTIR, as shown in FIG. 19, infrared light is applied from an infrared light source 100 to a gas-to-be-monitored. Then, the infrared light which has passed through the gas-to-be-monitored is spectroscopically analyzed by a spectroscope 102, and absorbance spectra are given. Infrared absorbance spectra are intrinsic to chemicals, which enables the chemicals in the gas-to-be-monitored to be identified. Absorbed amounts of the infrared light are proportional to concentration of chemicals, which enables the quantities of chemicals in the gas-to-be-monitored to be determined. The FTIR is simpler in the device structure than the GC-MS and takes a shorter period of time for the measurement. The FTIR is a real time measuring method. Furthermore, advantageously, the FTIR is brought into an environment to be monitored and can monitor the environment at the site.

However, the GC-MS takes several hours for the usual measurement. From the viewpoint of environmental monitoring, the GC-MS is not usable in real time. Columns used in the GC-MS must be prepared in laboratories, and cannot monitor the environment at the site. Thus, it is difficult to effectively feed the back monitored results to environmental control, etc.

On the other hand, disadvantageously the FTIR is difficult to monitor atmospheric environments with high sensitivity. Generally, when an atmospheric environment is monitored by FTIR, as described above, the infrared light source and the spectroscope are installed in the atmospheric environment to be monitored, and infrared light is applied directly to the atmosphere to spectroscopically analyze the infrared light.

In this case, a monitoring sensitivity of the FTIR to chemical present in a gas is proportional to an optical path length of the applied infrared light. For example, to detect a chemical present in an about 1 ppm concentration in a gas, an optical path length of the infrared light must be about 1 m. Thus, in order to detect a trace of a chemical which is present in an atmosphere only in a concentration ratio of 0.01 ppm, i.e., with higher sensitivity, even a 100 m-optical path length of the infrared light is required. In other words, in order to detect traces of chemicals by the FTIR, a large-scale optical system which ensures the optical path length of the infrared light is required. Thus, in realizing the detection of traces of chemicals in atmospheres by the FTIR, the advantage of the FTIR that the FTIR can be installed at site and can measure in real time is spoiled.

DISCLOSURE OF INVENTION

An object of the present invention is to provide a chemical detecting method and apparatus which can detect chemicals present in an environment at high speed and with high sensitivity.

The above-described object is achieved by a chemical detecting method comprising: exposing a substrate for a chemical to be adsorbed to, to a gas-to-be-monitored; enhancing the adsorption of the chemical contained in the gas-to-be-monitored to the substrate; applying an infrared light to the substrate with the chemical adsorbed to; analyzing the infrared light which has passed through and exited the substrate or has been reflected on the surface of the substrate to thereby identify a kind of the chemical adsorbed to the substrate and/or compute an adsorption amount of the chemical; and identifying a kind of the chemical in the gas-to-be-monitored and/or computing a concentration of the chemical, based on the amount of the chemical adsorbed to the substrate.

In the above-described chemical detecting method, it is possible that the substrate is cooled to thereby enhance the adsorption of the chemical in the gas-to-be-monitored to the substrate.

In the above-described chemical detecting method, it is possible that the substrate is exposed to the gas-to-be-monitored after a relative humidity of the gas-to-be-monitored has been decreased.

In the above-described chemical detecting method, it is possible that the gas-to-be-monitored is desiccated to decrease a relative humidity of the gas-to-be-monitored.

In the above-described chemical detecting method, it is possible that the gas-to-be-monitored is mixed with a desiccating gas to decrease a relative humidity of the gas-to-be-monitored.

In the above-described chemical detecting method, it is possible that a concentration of the chemical in the gas-to-be-monitored is computed in consideration of a concentration of the chemical which has been decreased corresponding to the decrease of the relative humidity of the gas-to-be-monitored.

In the above-described chemical detecting method, it is possible that the gas-to-be-monitored is flowed with respect to the surface of the substrate to enhance the adsorption of the chemical in the gas-to-be-monitored to the substrate.

In the above-described chemical detecting method, it is possible that the substrate is housed in a vessel having an inlet port and an outlet port, and the gas-to-be-monitored is fed into the vessel through the inlet port and discharged through the outlet port to thereby flow the gas-to-be-monitored.

In the above-described chemical detecting method, it is possible that the substrate is formed of a substance which transmits the infrared light; and the infrared light which has made multiple reflections in the substrate and exited the substrate is analyzed to identify a kind of the chemical adsorbed to the substrate and/or compute an adsorption amount of the chemical.

In the above-described chemical detecting method, it is possible that the substrate is formed of a substance which transmits the infrared light; and the infrared light which has been incident on one surface of the substrate and exited the substrate at the other surface is analyzed to thereby identify a kind of the chemical adsorbed to the substrate and/or compute an adsorption amount of the chemical.

In the above-described chemical detecting method, it is possible that the substrate comprises a pair of substrates which are arranged substantially in parallel with each other; and the infrared light which has made multiple reflections between the pair of substrates and exited the substrate to thereby identify a kind of the chemical adsorbed to the substrate and/or compute an adsorption amount of the chemical.

In the above-described chemical detecting method, it is possible that the chemical adsorbed to the substrate is periodically removed to initialize a surface state of the substrate.

In the above-described chemical detecting method, it is possible that the substrate is heated to remove the chemical adsorbed to the substrate.

In the above-described chemical detecting method, it is possible that an ultraviolet radiation is applied to the substrate to remove the chemical adsorbed to the substrate.

The above-described object is also achieved by a chemical detecting apparatus comprising: a substrate for a chemical in a gas-to-be-monitored to be adsorbed to; an adsorption rate improving means for enhancing the adsorption of the chemical in the gas-to-be-monitored to the substrate; an infrared application means for applying an infrared light to the substrate with the chemical adsorbed to; an infrared analyzing means which analyzes the infrared light exiting the substrate after passed through the substrate to thereby identify a kind of the chemical adsorbed to the substrate and/or compute an adsorption amount of the chemical; and a chemical detecting means which identifies a kind of the chemical in the gas-to-be-monitored and/or compute an adsorption amount of the chemical, based on an analysis result given by the infrared analyzing means.

In the above-described chemical detecting apparatus, it is possible that the substrate is formed of a substance transmitting the infrared light; and the infrared analyzing means analyzes the infrared light which has made multiple reflections in the substrate and exited the substrate to thereby identify a kind of the chemical adsorbed to the substrate and/or compute an adsorption amount of the chemical.

In the above-described chemical detecting apparatus, it is possible that the substrate is formed of a substance which transmits the infrared light; and the infrared analyzing means analyzes the infrared light which has been incident on one surface of the substrate, passed through the substrate and exited the other surface of the substrate to thereby identify a kind of the chemical adsorbed to the substrate and/or compute an adsorption amount of the chemical.

In the above-described chemical detecting apparatus, it is possible that the substrate comprises a pair of substrate which are arranged substantially in parallel with each other; and the infrared analyzing means analyzes the infrared light which has made multiple reflections between the pair of substrates and exited the substrate to thereby identify a kind of the chemical adsorbed to the substrate and/or compute an adsorption amount of the chemical.

In the above-described chemical detecting apparatus, it is possible that the adsorption rate improving means is a cooling device for cooling the substrate.

In the above-described chemical detecting apparatus, it is possible that the cooling device cools a part of the substrate, which is not an optical path of the infrared light.

In the above-described chemical detecting apparatus, it is possible that the apparatus further comprises a humidity decreasing means which decreases a relative humidity of the gas-to-be-monitored.

In the above-described chemical detecting apparatus, it is possible that the humidity decreasing means is a filter for desiccating the gas-to-be-monitored.

In the above-described chemical detecting apparatus, it is possible that the humidity decreasing means comprises a cooling means which cools the gas-to-be-monitored before arriving at the infrared transmitting substrate, and the inside of the cooling means is dewed to thereby desiccate the gas-to-be-monitored to decrease a relative humidity of the gas-to-be-monitored.

In the above-described chemical detecting apparatus, it is possible that the humidity decreasing means mixes the gas-to-be-monitored with a desiccating gas to thereby decrease a relative humidity of the gas-to-be-monitored.

In the above-described chemical detecting apparatus, it is possible that the apparatus further comprises a vessel housing the substrate; and a gas flowing means which makes the gas-to-be-monitored flow in the vessel.

In the above-described chemical detecting apparatus, it is possible that the apparatus further comprises a substrate purifying means which removes the chemical adsorbed to the surface of the substrate to initialize a surface state of the substrate.

In the above-described chemical detecting apparatus, it is possible that the substrate purifying means heats the substrate to remove the chemical adsorbed to the substrate.

In the above-described chemical detecting apparatus, it is possible that the substrate purifying means applies an ultraviolet radiation to the surface of the substrate to remove the chemical adsorbed to the substrate.

According to the present invention, the substrate for chemicals to be adsorbed to is exposed in a gas-to-be-monitored, the adsorption of the chemicals in the gas-to-be-monitored to the substrate is enhanced, an infrared light is applied to the substrate with the chemicals adsorbed to, the infrared light which has passed through the substrate and exited the substrate or which has reflected on the surface of the substrate is analyzed to thereby identify kinds of the chemicals adsorbed to the substrate and/or compute adsorption amounts of the chemicals, based on the adsorption amounts of the chemicals adsorbed to the substrate, kinds of the chemicals in the gas-to-be-monitored are identified and/or concentrations of the chemicals are computed, whereby chemicals present in an environment can be detected at high speed and with high sensitivity.

BEST MODE FOR CARRYING OUT THE INVENTION

Principle of the Present Invention

Figure 1:
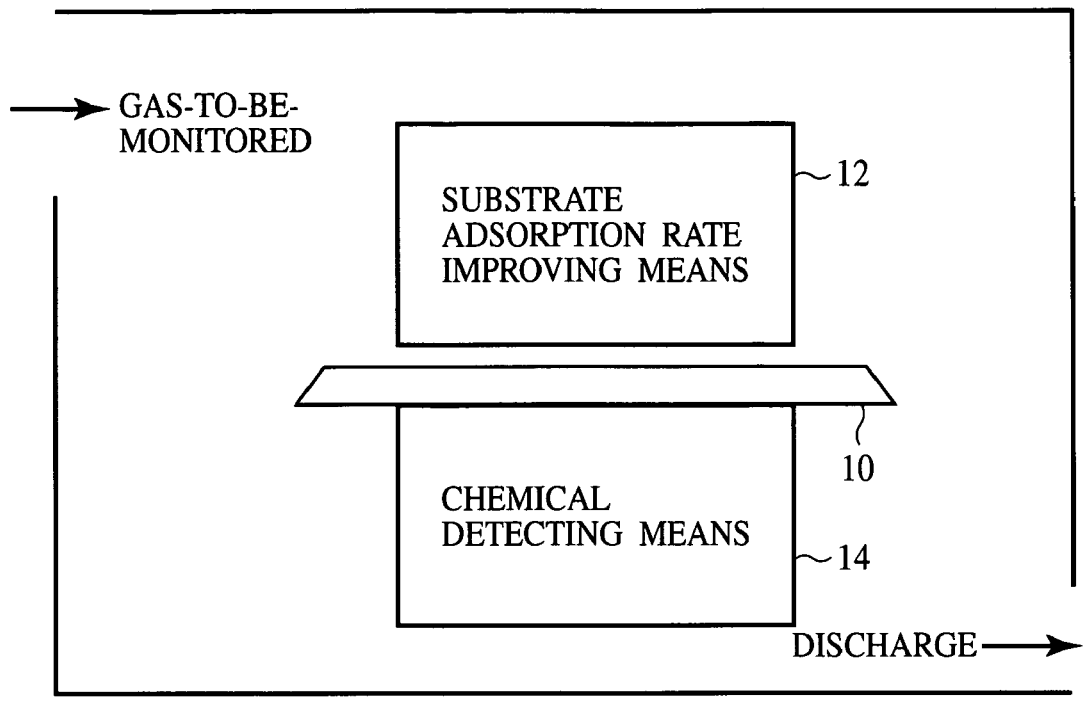
FIG. 1 is a diagrammatic view showing the principle of the chemical detecting method and apparatus according to the present invention.
Figure 2:
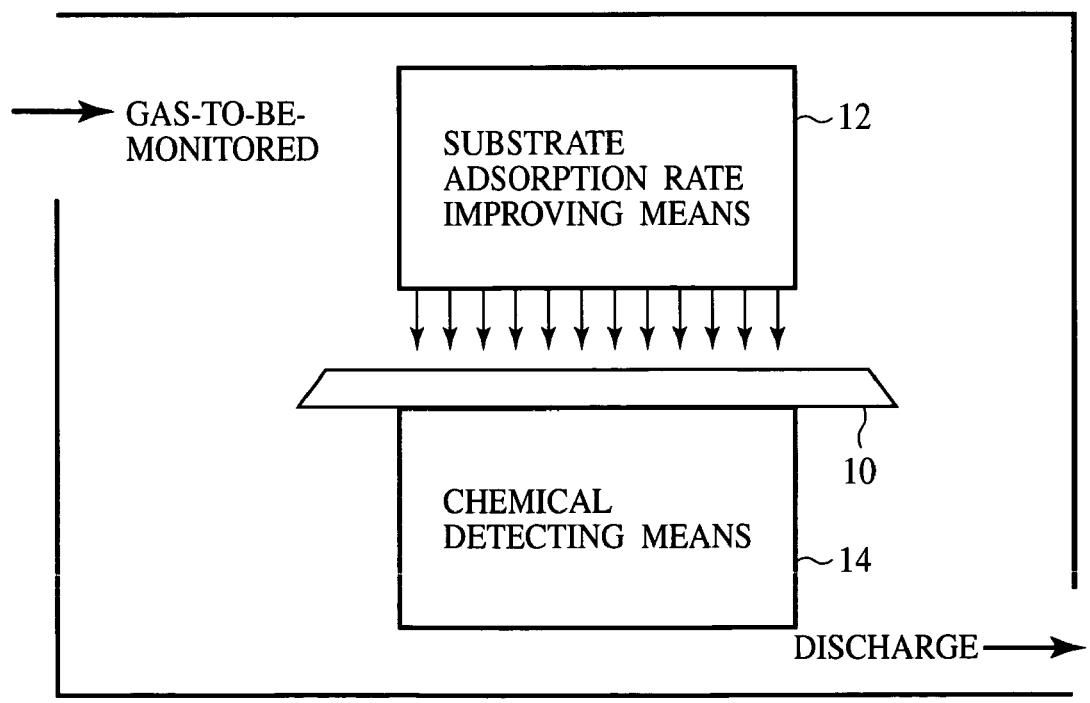
FIG. 2 is a diagrammatic view of an example of a substrate adsorption rate improving means of the chemical detecting apparatus according to the present invention.
Figure 3:
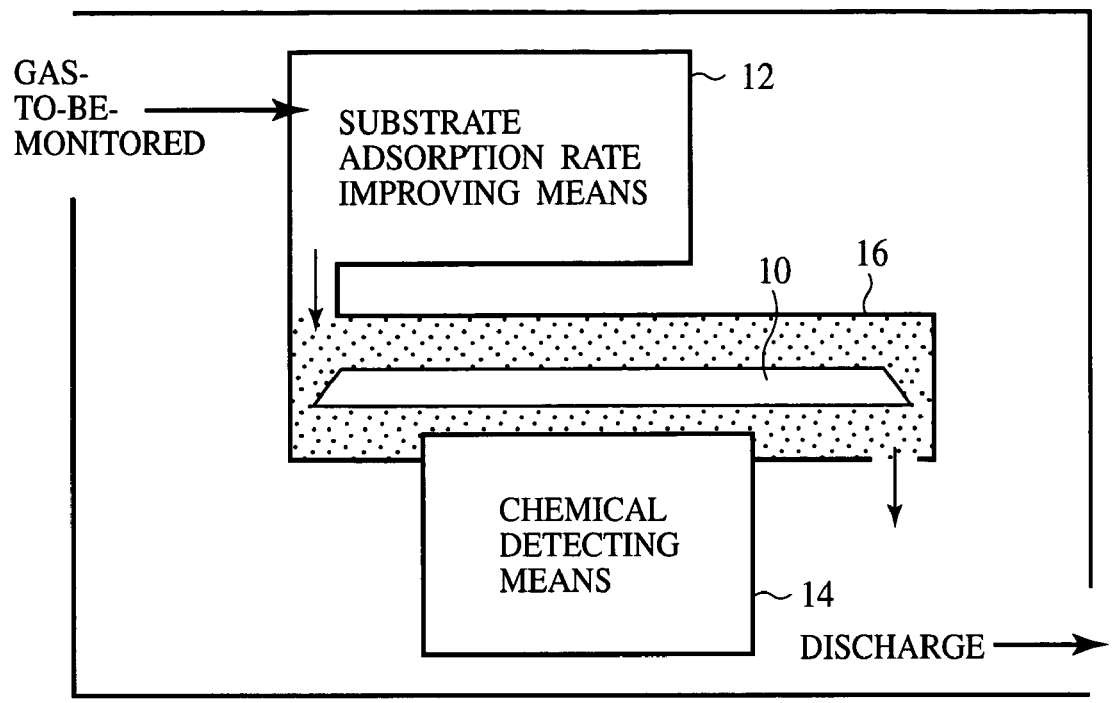
FIG. 3 is a diagrammatic view of an example of a substrate adsorption rate improving means of the chemical detecting apparatus according to the present invention.
Figure 4:
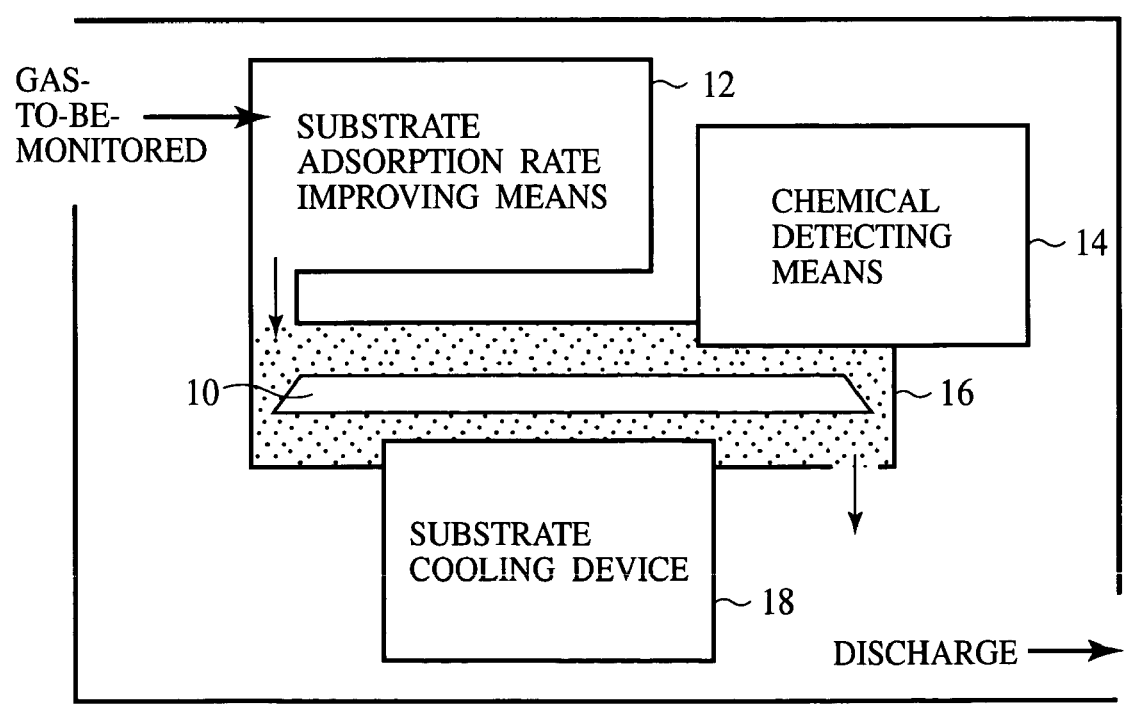
FIG. 4 is a diagrammatic view of an example of a substrate adsorption rate improving means of the chemical detecting apparatus according to the present invention.
Figure 5:
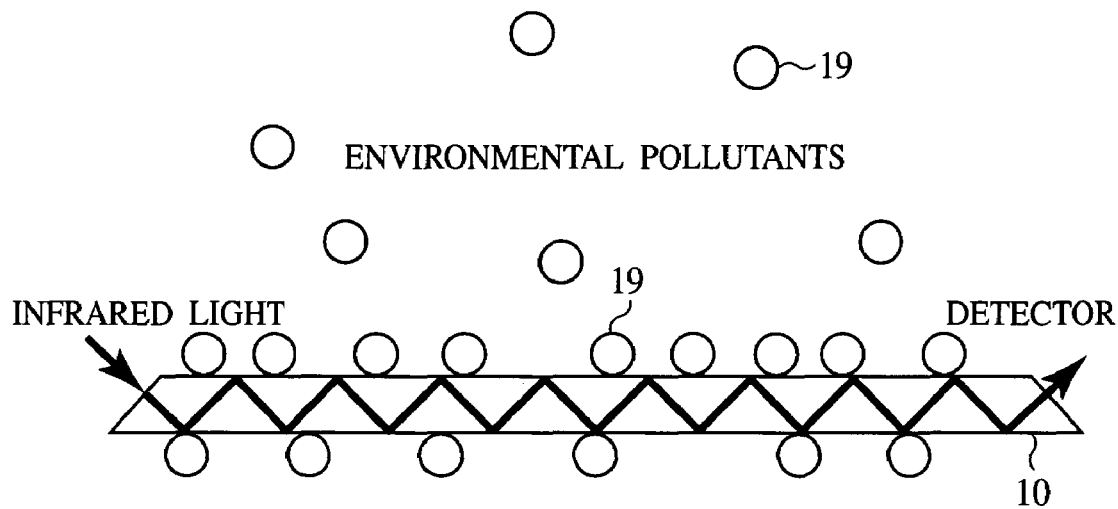
FIG. 5 is a diagrammatic view explaining the principle of detecting chemicals adsorbed to the substrate surface by infrared multiple internal reflection method.
Figure 6:
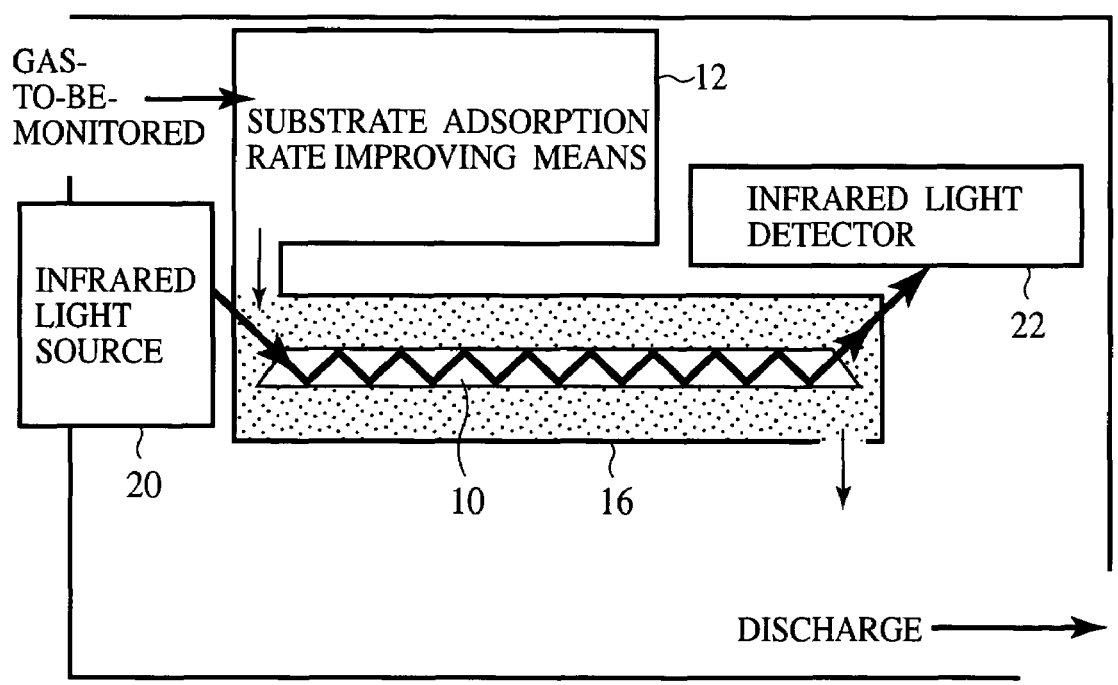
FIG. 6 is a diagrammatic view of an example of a chemical detecting means of the chemical detecting apparatus according to the present invention.
Figure 7:
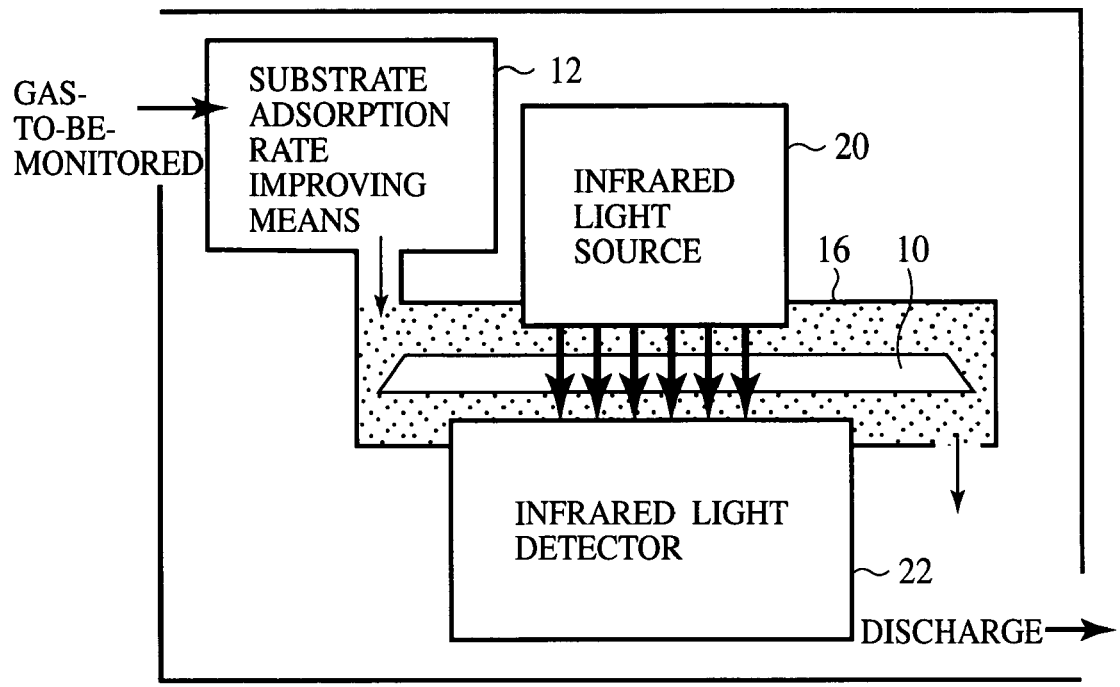
FIG. 7 is a diagrammatic view of an example of a chemical detecting means of the chemical detecting apparatus according to the present invention.
Figure 8:
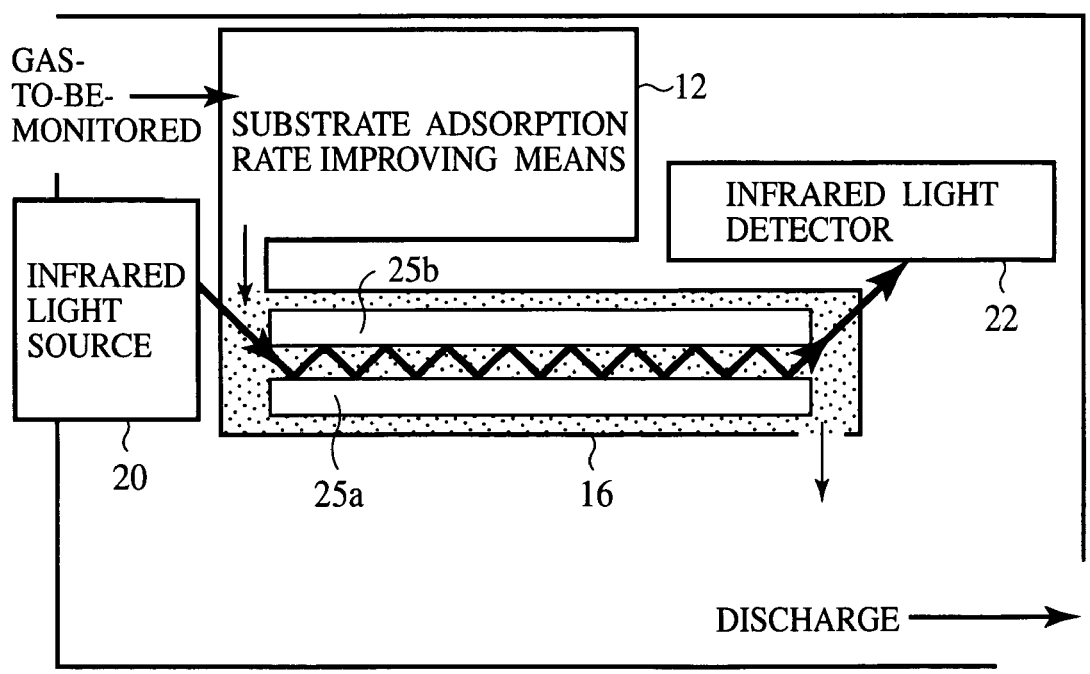
FIG. 8 is a diagrammatic view of an example of a chemical detecting means of the chemical detecting apparatus according to the present invention.

The principle of the chemical detecting method and apparatus according to the present invention will be explained with reference to FIGS. 1 to 7. FIG. 1 is a diagrammatic view explaining the principle of the chemical detecting method and apparatus according to the present invention. FIGS. 2 to 4 are diagrammatic views explaining examples of a substrate adsorption rate improving means. FIG. 5 is a diagrammatic view of the principle of detecting chemicals adsorbed to the substrate surface by infrared multiple internal reflection method. FIGS. 6 to 8 are diagrammatic views of examples of a chemical detecting means.

As shown in FIG. 1, the chemical detecting apparatus according to the present invention comprises, as basic constituent elements, a substrate 10 for adsorbing chemicals in a gas-to-be-monitored, a substrate adsorption rate improving means 12 which improves the rate of adsorption of the chemical to the surface of the substrate 10, and a chemical detecting means 14 which identifies kinds of the chemicals adsorbed to the surface of the substrate 10 and/or computes adsorption amounts of the chemicals.

First, the substrate adsorption rate improving means 12 will be explained with reference to FIGS. 2 to 4.

The chemical detecting method and apparatus according to the present invention analyze chemicals adsorbed to the surface of the substrate 10 exposed in a gas-to-be-monitored to detect the chemicals in the gas-to-be-monitored. Accordingly, to realize the detection of chemicals with higher sensitivity than the conventional art, it is necessary to make the chemicals adsorbed to the surface of the substrate 10 in a concentrated state. The substrate adsorption rate improving means 12 is for making the chemicals adsorbed to the surface of the substrate 10 in the concentrated state.

As shown in FIG. 2, the substrate adsorption rate improving means 12 comprises a means which makes a gas-to-be-monitored flow to the surface of the substrate 10. For example, a fan or the like can be the substrate adsorption rate improving means 12. Thus, chemicals in a gas-to-be-monitored impinge on the surface of the substrate 10 with a higher probability. Resultantly, the chemicals can be effectively adsorbed to the surface of the substrate 10.

As shown in FIG. 3, it is possible that the substrate 10 is housed in a substrate sealing vessel 16, and the substrate adsorption rate improving means 12 lets a gas-to-be-monitored into and out of the substrate sealing vessel 16. Thus, the gas-to-be-monitored can flow near the surface of the substrate 10. Resultantly, the efficiency of adsorption of chemicals in the gas-to-be-monitored to the surface of the substrate 10 can be improved.

The substrate cooling device 18 for cooling the substrate 10 is provided in addition to the substrate adsorption rate improving means 12 as shown in FIG. 4 or singly, whereby the efficiency of adsorption of chemicals to the surface of the substrate can be improved.

Generally, chemicals are cooled to change the states from gas to liquid and from liquid to solid. When chemicals freely moving in a gas-to-be-monitored impinge on the substrate 10, parts of the chemicals are trapped on the surface of the substrate 10. At this time, when no temperature difference is present between the gas-to-be-monitored and the substrate 10, most of the trapped chemicals leave again the surface. However, when the substrate 10 is cooled, energies of the chemicals are deprived upon the impingement on the surface of the substrate 10, and the chemicals cannot leave again the surface of the substrate 10. With higher probability the chemicals remain trapped on the surface of the substrate. That is, the substrate 10 is cooled, whereby total amounts of chemicals adsorbed to the surface of the substrate 10 can be increased.

Then, the chemical detecting means 14 will be explained with reference to FIGS. 5 to 8.

The chemical detecting means 14 identifies kinds of chemicals of a gas-to-be-monitored adsorbed to the surface of the substrate 10 and/or computes adsorbed amounts of the chemicals. Based on the monitored results of the chemicals adsorbed to the surface of the substrate 10 obtained by the chemical detecting means 14, kinds of the chemicals in the gas-to-be-monitored can be identified and/or abundances of the chemicals can be computed.

Various means for detecting chemicals are considered. The detection method using infrared light is preferable in consideration of the real time monitoring, simplicity, etc.

As a detection method using infrared light, Fourier transform infrared spectroscopy (FTIR) which detects chemicals by analyzing absorbance spectra of infrared light can be used.

Furthermore, in the present invention, chemicals adsorbed to the surface of the substrate 10 are detected, and an infrared multiple internal reflection method, for example, can be used. The principle of detecting chemicals adsorbed to the substrate surface by the infrared multiple internal reflection method will be explained with reference to FIG. 5.

When the substrate 10 of a material which transmits infrared light is exposed in the gas-to-be-monitored, as shown in FIG. 5, chemicals, such as environmental pollutants 19, etc. in the gas-to-be-monitored are adsorbed to the surface of the substrate 10. Then, infrared light is applied to the end surface of the substrate 10 to make multiple reflections inside the substrate 10. While the infrared light is repeating the multiple reflections inside the substrate 10, that of the infrared light penetrating (evanescent light) when the infrared light is reflected on the surface of the substrate 10 has frequency components which are equal to molecular vibration frequencies of environmental chemicals, the absorption of the infrared light takes place. The infrared light which is attenuated by T times by the absorption upon one reflection on the surface is expressed by Lambert-Beer Formula $$T=(I/I_0)e^{-Ac}$$

wherein $I_0$ and I represent light reflection intensities before and after a chemical is adsorbed to the surface; c represents a concentration of an organic substance on the surface; and A represents a constant.

The infrared absorption described above is intrinsic to structures of molecules. Accordingly, the infrared light exiting after the multiple reflections in the substrate 10 is spectroscopically analyzed, whereby kinds and/or adsorption amounts of environmental pollutants 19 adsorbed to the surface of the substrate 10 in a gas-to-be-monitored can be detected. Based on a result of the measurement, identification of kinds and/or computation of concentrations of environmental pollutants 19 in the gas-to-be-monitored can be performed.

The above-described method has advantages that no complicated pre-treatments of samples are required, the measurement is conducted in real time, and the measurement does not take much time, and other advantages. The infrared light which has repeated multiple reflections is spectroscopically analyzed, which improves the signal vs. noise ratio (S/N ratio), and chemicals, such as environmental pollutants, etc. can be detected with high sensitivity.

The chemical detecting method using the above-described infrared multiple internal reflection method is detailed in, e.g., the specification of Japanese Patent Application No. Hei 11-231495 (1999). The FTIR is detailed in, e.g., N. B. Colthup, L. H. Daly, and S. E. Wiberley, "Introduction to Infrared and Raman Spectroscopy" (Academic Press).

FIG. 6 is a diagrammatic view of the chemical detecting apparatus comprising the substrate adsorption rate improving means 12, and the chemical detecting means 14 using the multiple internal reflection FTIR method. As shown, the infrared light source 20 which applies infrared light to the substrate 10 as probe light is disposed near one end surface of the substrate 10 housed in the substrate sealing vessel 16. The infrared light from the infrared light source 20 is incident so that the infrared light makes multiple reflections in the substrate 10. The infrared light detector 22 which detects the infrared light exiting the substrate 10 after the multiple reflections inside the substrate 10 is disposed near the end surface opposed to the end surface of the substrate 10, near which the infrared light source 20 is disposed. The infrared light detector 22 can be, e.g., an FTIR apparatus, which makes Fourier transform spectroscopy on the incident infrared light.

The chemical detecting means 14 may radiate the infrared light to the surface of the substrate 10, and detect and spectroscopically analyze the infrared light which has passed through the substrate 10. FIG. 7 is a diagrammatic view of the chemical detecting apparatus comprising the substrate adsorption rate improving means 12 shown in FIG. 3, and the chemical detecting means which detect the chemicals by spectroscopically analyzing the infrared light which has passed through the substrate 10. As shown, the infrared light source 20 which applies the infrared light to the surface of the substrate 10 is disposed near one surface of the substrate 10 housed in the substrate sealing vessel 16. The infrared light detector 22 which detects and spectroscopically analyzes the infrared light which has passed through the substrate 10 is disposed near the surface of the substrate 10 opposed to the surface which is near the infrared light source 20 is disposed.

The chemical detecting means 14 does not essentially use the above-described infrared multiple internal reflection method or others but may use ATR (Attenuated Total Reflection) method. FIG. 8 is a diagrammatic view of the chemical detecting apparatus comprising the chemical detecting means 14 using the ATR method. As shown, a pair of substrates 25a, 25b which are arranged substantially in parallel with each other is housed in the substrate sealing vessel 16. The infrared light source 20 is disposed near one end surfaces of the substrates 25a, 25b so that the infrared light as probe light is incident between the substrates 25a, 25b. The infrared light from the infrared light source 20 is applied so that the infrared light makes multiple reflections between the opposed substrates 25a, 25b. The infrared light detector 22 which detects and spectroscopically analyzes the infrared light which has made multiple reflections between the opposed substrates 25a, 25b and exited is disposed near the other end surfaces of the substrates 25a, 25b, which are opposed to one end surfaces.

As described above, the chemical detecting method and apparatus according to the present invention is characterized in that the substrate adsorption improving means 12 makes large amounts of chemicals in a gas-to-be-monitored adsorbed to the surface of the substrate 10, and the chemicals adsorbed to the surface of the substrate 10 are detected by the chemical detecting means 14 using infrared light. Such chemical detecting method and apparatus can realize the detection of traces of chemicals present in atmospheric environments with high sensitivity.

The chemical detecting method and apparatus according to the present invention can concurrently sample and detect chemicals in the gas-to-be-monitored, in other words, it can monitor the gas in real time. Accordingly, the monitoring time can be much shorter in comparison with the monitoring method using the conventional GC-MS. In a typical monitoring example, the monitoring using the conventional GC-MS requires several hours of monitoring time, while the present invention can detect chemicals, such as dioxine, etc. in several minutes to about 10 minutes of monitoring time.

FIRST EMBODIMENT

Figure 9:
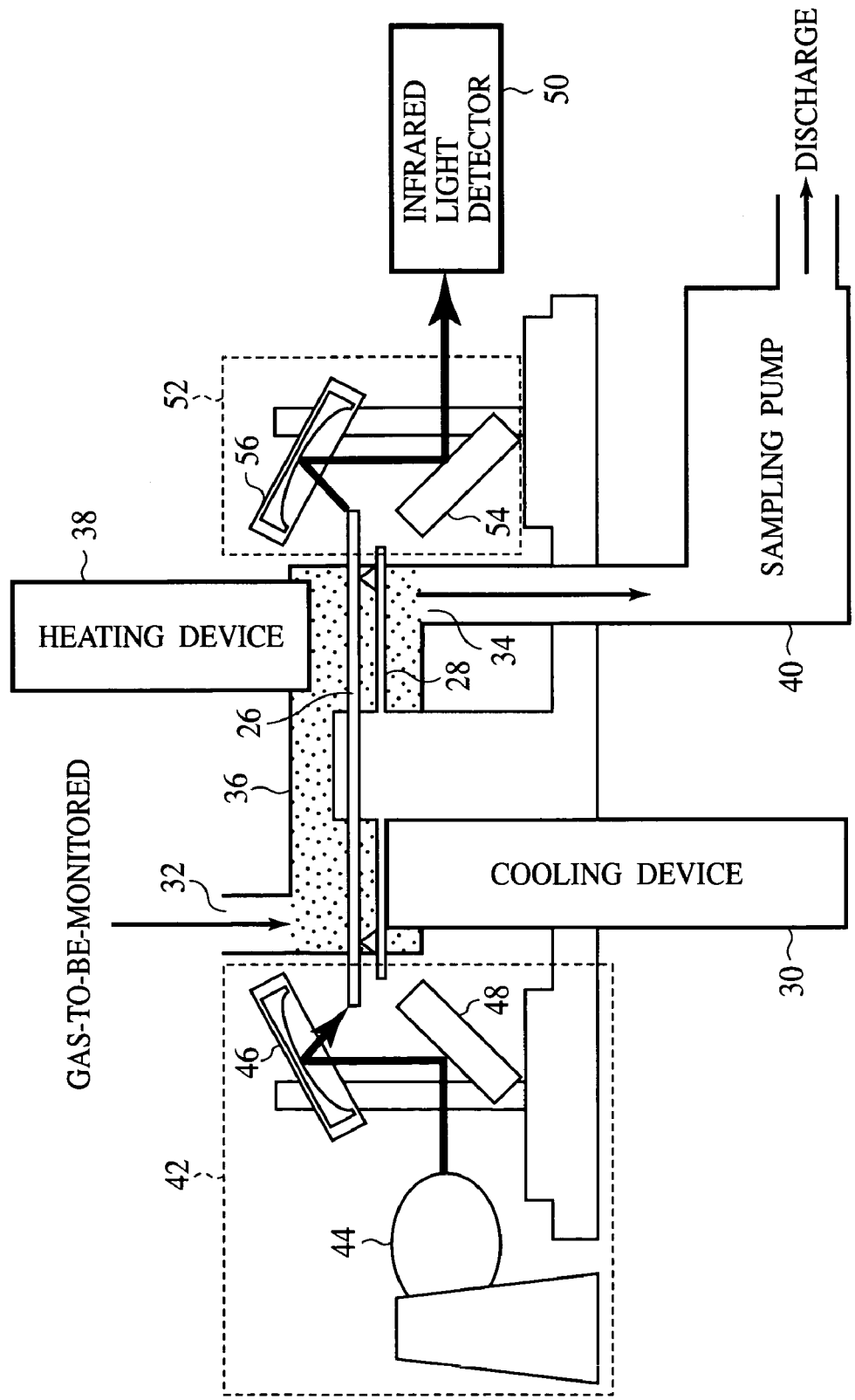
FIG. 9 is a sectional view of the chemical detecting apparatus according to a first embodiment of the present invention, which shows a structure thereof.
Figure 10:
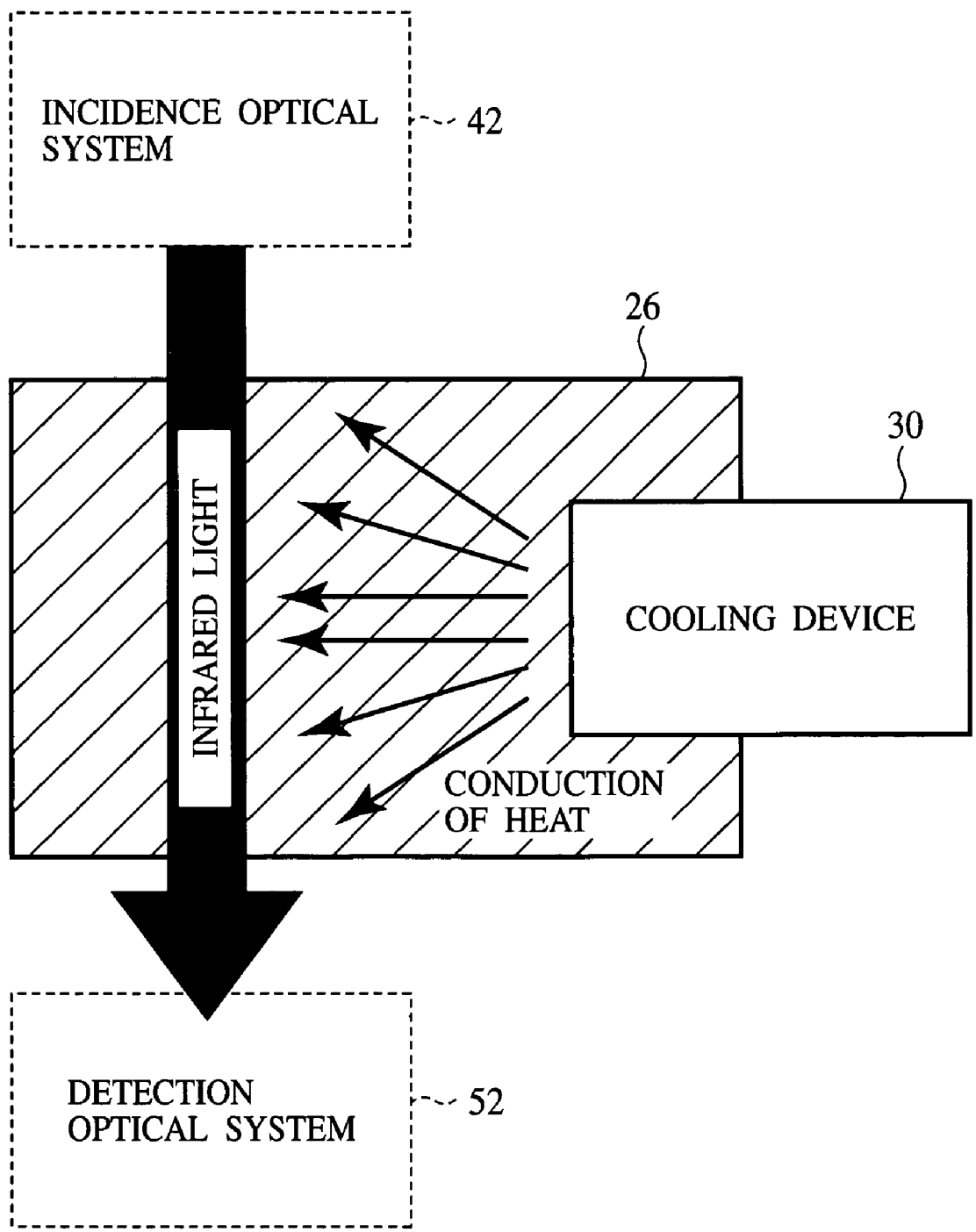
FIG. 10 is a diagrammatic view of one example of the method for cooling the infrared transmitting substrate by a cooling device of the chemical detecting apparatus according to the first embodiment of the present invention.
Figure 11:
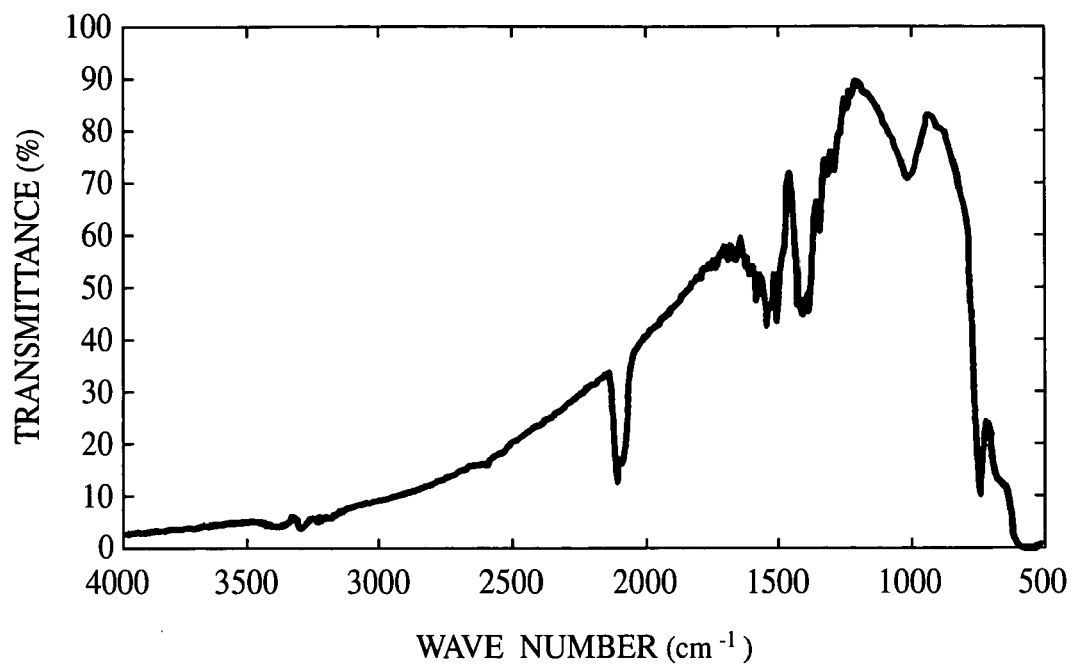
FIG. 11 is a graph of infrared transmission spectrum of GaAs.
Figure 12:
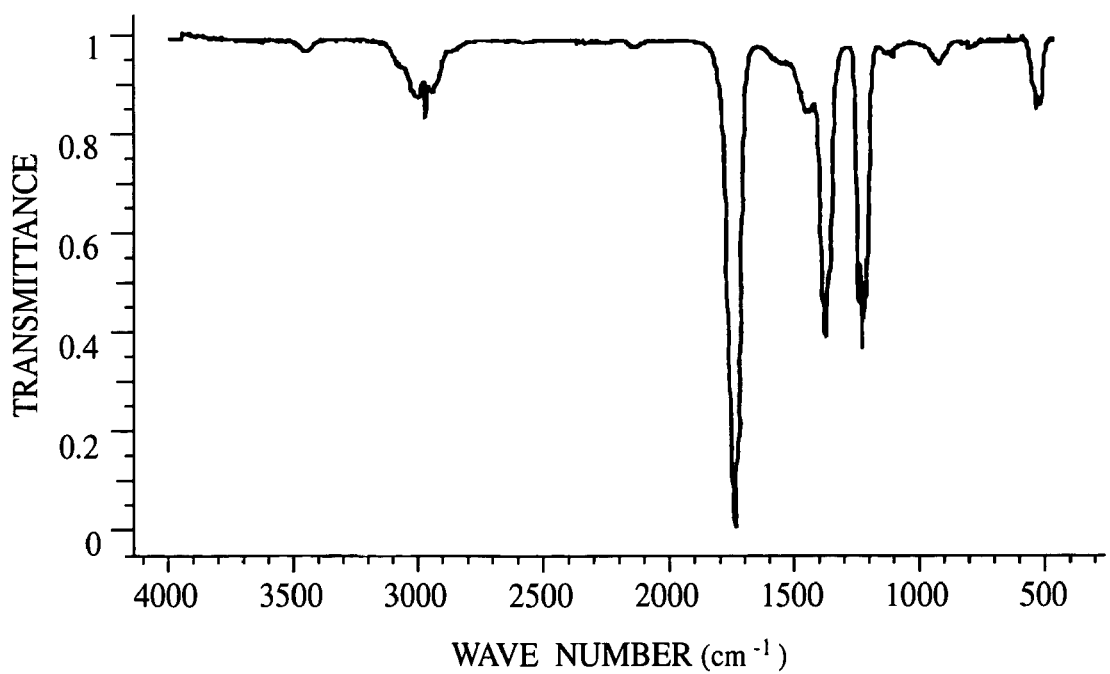
FIG. 12 is infrared absorbance spectrum of an acetone standard sample.
Figure 13:
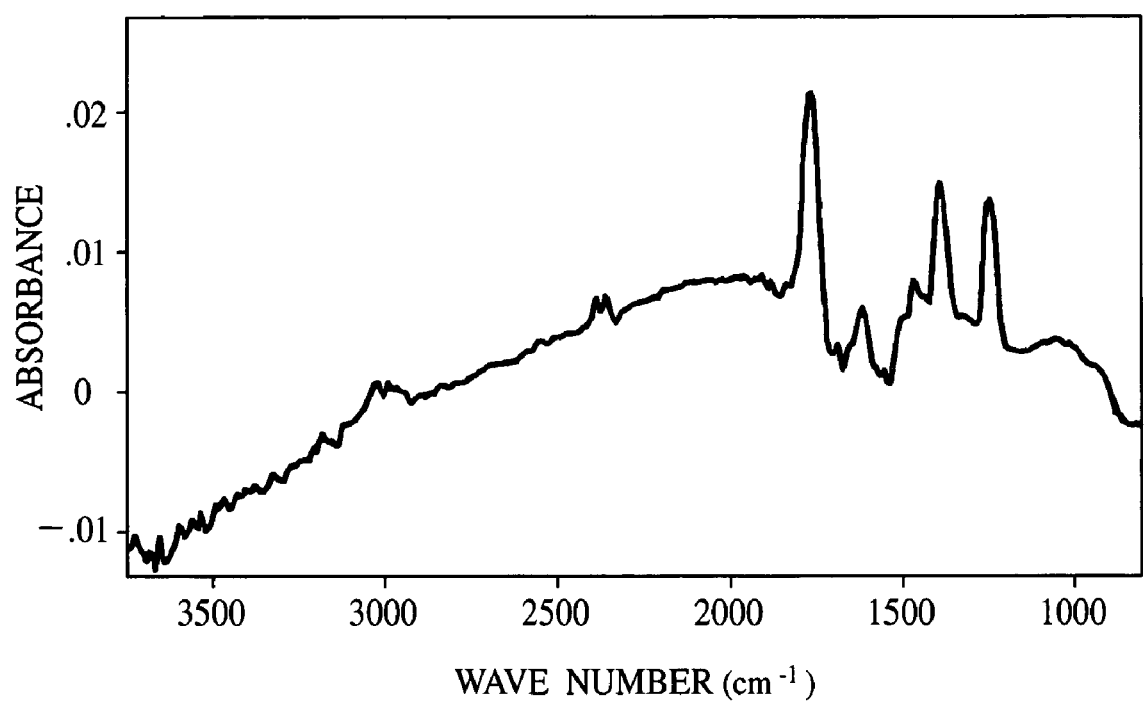
FIG. 13 is a graph of spectrum showing a detecting result of acetone given by the chemical detecting method according to the first embodiment of the present invention.

Then, the chemical detecting method and apparatus according to a first embodiment of the present invention will be explained with reference to FIGS. 9 to 13. FIG. 9 is a sectional view of the chemical detecting apparatus according to the present embodiment. FIG. 10 is a plan view of one example of the methods for cooling the infrared transmitting substrate by the cooling device. FIG. 11 is an infrared transmission spectrum of GaAs, which is an infrared transmitting crystal. FIG. 12 is an infrared absorbance spectrum of an acetone standard sample. FIG. 13 is a spectrum of a monitoring result of acetone present in the atmosphere monitored by the chemical detecting apparatus.

[1] The Chemical Detecting Apparatus

First, the chemical detecting apparatus according to the present embodiment will be explained with reference to FIGS. 9 and 10.

As shown in FIG. 9, in the chemical detecting apparatus according to the present embodiment, an infrared transmitting substrate 26 to which chemicals in a gas-to-be-monitored is adsorbed to be monitored is placed on a mount 28. A cooling device 30 is provided in the mount 28 to cool the infrared transmitting substrate 26.

The infrared transmitting substrate 26 is sealed in a substrate sealing vessel 36 having an inlet port 32 through which a gas-to-be-monitored is fed, and an outlet port through which the gas-to-be-monitored is discharged, and end surfaces of the infrared transmitting substrate 26 opposed to each other are exposed to the outside through both side of the substrate sealing vessel 36.

A heating device 38 is provided in the substrate sealing vessel 36 to heat the whole substrate sealing vessel 36 including the infrared transmitting substrate 26. A sampling pump 40 for making a gas-to-be-monitored flow in the substrate sealing vessel 36 is connected to the outlet port 34 of the substrate sealing vessel 36.

An incidence optical system 42 is arranged near one of the end surfaces exposed outside the substrate sealing vessel 36 of the infrared transmitting substrate 26. The incidence optical system 42 comprises an infrared light source 44 which emits infrared light as probe light, a reflection mirror 48 which leads the infrared light emitted by the infrared light source 44, and a concave mirror 46 which condenses the infrared light led by the reflection mirror 48 to lead the infrared light from the end surface of the infrared transmitting substrate 26 into the interior of the infrared transmitting substrate 26 so that the infrared light makes multiple reflections.

An infrared light detector 50 for detecting the transmitted infrared light which has made multiple reflections in the infrared transmitting substrate 26 and exited the infrared transmitting substrate 26 is disposed near the end surface of the infrared transmitting substrate 26 opposed to the end surface near which the incidence optical system 42 is disposed, via a detection optical system 52. The detection optical system 52 comprises a concave mirror 56 which condenses the infrared light exiting the end surface of the infrared transmitting substrate 26 and leads the infrared light to a reflection mirror 54, and the reflection mirror 54 which leads the infrared light led by the concave mirror 56 to the infrared light detector 50. The infrared light detector 50 is, e.g., an FTIR (Fourier transform infrared spectrochemical analysis) apparatus which spectroscopically analyzes incident infrared light.

The infrared light detector 50, which is, e.g., an FTIR apparatus, is connected to a computer and display (not shown) which identifies kinds of chemicals in a gas-to-be-monitored and computes concentrations of the chemicals.

As described above, the chemical detecting apparatus according to the present embodiment uses as substrate adsorption rate improving means the sampling pump 40 which makes a gas-to-be-monitored flow in the substrate sealing vessel 36, and also the cooling device 30. The chemical detecting apparatus according to the present embodiment uses as the chemical detecting means for detecting chemicals adsorbed to the surface of the infrared transmitting substrate 26, multiple internal reflection FTIR method.

Next, the respective constituent elements of the chemical detecting apparatus according to the present embodiment will be detailed below.

(a) Infrared Transmitting Substrate 26

The infrared transmitting substrate 26 adsorbs chemicals in a gas-to-be-monitored to be used in measuring the chemicals. Accordingly, the infrared transmitting substrate 26 must be formed of a material which transmits light of a frequency range corresponding to molecular vibrations of chemicals to be detected. A wave number range corresponding to the basic vibrations of typical organic substances is the middle infrared/near infrared range of about 500 $cm^{-1}$ (wavelength: 20 μm)–5000 $cm^{-1}$ (wavelength: 2 μm). A material which transmits at least a wave number range of the infrared absorption caused by a specific kind of molecular vibrations common with substances, which (a wave number range) is in the wave number range of the infrared absorption of the organic substances, e.g., which transmits at least a wave number range corresponding to $CH_3$ asymmetric stretching vibrations is selected for the infrared transmitting substrate 26. As the infrared transmitting substrate 26 is exposed to the atmosphere in detecting chemicals, it is necessary that a material of the infrared transmitting substrate 26 has no deliquescence.

For example, gallium arsenic (GaAs), which has a transmission wavelength range of about 1.0-18 μm and is a stable substance in the atmosphere, can be selected as one material forming the infrared transmitting substrate 26. In addition to gallium arsenic, zinc selenide (ZnSe: 0.6-13 μm transmission wavelength range), silicon (Si: 1.2-6 μm transmission wavelength range), potassium bromide (KBr: 0.4-22 μm transmission wavelength range), calcium fluoride ($CaF_2$: 0.2-8 μm transmission wavelength range), germanium (Ge: 2-18 μm transmission wavelength range), etc. can be selected as materials of the infrared transmitting substrate 26.

It is preferable that the infrared transmitting substrate 26 has a configuration having the end surfaces tilted at e.g. 45°. Such configuration can increase the incidence efficiency of the infrared light into the infrared transmitting substrate 26 and can cause the infrared light to make multiple reflections in the infrared transmitting substrate 26. The infrared transmitting substrate 26 must be a substrate having both surfaces polished to prevent the infrared light from scattering when the infrared light makes multiple internal reflections.

(b) Mount 28

The infrared transmitting substrate 26 is placed on the mount 28. An arrangement for the back surface of the infrared transmitting substrate 26 not to be in complete close contact with the mount 28 may be made so that chemicals in a gas-to-be-monitored to be adsorbed not only to the upper surface of the infrared transmission substrate 26 but also to the back surface of the infrared transmission substrate 26. For example, a plurality of convex structures may be formed on the mounting surface of the mount 28 to mount the infrared transmitting substrate 26 on the convex structures. The infrared transmitting substrate 26 is set in a condition where the back surface of the infrared transmitting substrate 26 is exposed to the gas-to-be-monitored. Thus, the infrared transmitting substrate 26 has the area for chemicals to be adsorbed increases, and the signal vs. noise ratio (S/N ratio) can be improved.

(c) Substrate Sealing Vessel 36 and Sampling Pump 40

The substrate sealing vessel 36 houses the infrared transmitting substrate 26, and a gas-to-be-monitored flow in the substrate sealing vessel 36 with the infrared transmitting substrate 26 housed in. Both end surfaces of the infrared transmitting substrate 26 are exposed outside through the opposed sides of the substrate sealing vessel 36, and the parts of the sides through which the end surfaces of the infrared transmitting substrate 26 are exposed outside are arranged to ensure gas tightness.

The sampling pump 40 discharges a gas in the substrate sealing vessel 36 through the outlet port 34 to regulate the interior condition of the substrate sealing vessel 36 to a negative pressure, so that a the gas-to-be-monitored is introduced into the substrate sealing vessel 36 through the inlet port 32 and discharged from the substrate sealing vessel 36 through the outlet port 34. The sampling pump 40 causes a gas-to-be-monitored to efficiently flow with respect to the surface of the infrared transmitting substrate 26. Thus, the adsorption range of chemicals in the gas-to-be-monitored to the surface of the infrared transmitting substrate 26 can be increased.

(d) Cooling Device 30

The cooling device 30 cools the infrared transmitting substrate 26 mounted on the mount 28 to raise the adsorption rate of chemicals in a gas-to-be-monitored to the surface of the infrared transmitting substrate 26.

The cooling device 30 may comprise a Peltier device, which is compact and requires no cooling material. The Peltier device is a cooling device using Peltier effect that a temperature gradient takes place when a current flow through the junction between different kinds of metals.

The cooling of the infrared transmitting substrate 26 by the cooling device 30 may rely on cooling the mount 28. Otherwise, as shown FIG. 10, the cooling device 30 may be bonded directly to the infrared transmitting substrate 26 for the cooling.

In the case that the infrared transmitting substrate 26 is cooled directly by the cooling device 30 using a Peltier effect device, a temperature of the whole infrared transmitting substrate 26 is lowered by about 30° C. than an ambient temperature. For example, when an ambient temperature is 20° C., the whole infrared transmitting substrate 26 is cooled down to about −10° C. In the case that the cooling device 30 is bonded directly to the infrared transmitting substrate 25, it is preferable that, as shown in FIG. 10, the cooling device 30 is bonded to a part of the surface of the infrared transmitting substrate 26, which is away from the optical path of the infrared light making multiple reflections in the infrared transmitting substrate 26. The region of the infrared transmitting substrate 26, which is the optical path of the infrared light, is cooled indirectly by the thermal conduction, whereby influence of the bonded surface on the infrared absorption can be prevented.

The infrared transmitting substrate 26 may be cooled by, in place of the cooling device 30 using the Peltier device, a cooler using dry ice or liquid nitrogen, or a cooler using a coolant used in refrigerators, etc. A cooling temperature for the infrared transmitting substrate 26 can be suitably adjusted corresponding to adsorption states, etc. of chemicals-to-be-detected to the infrared transmitting substrate 26.

(e) Heating Device 38

The heating device 38 is, e.g., an electric heater and heats the infrared transmitting substrate 26 and the substrate sealing vessel 36 to remove chemicals adsorbed to the surfaces of the infrared transmitting substrate 26 and the substrate sealing vessel 36. Thus, the surface of the infrared transmitting substrate 26 can be initialized, i.e., cleaned, whereby fresh monitoring can be performed without being influenced by the previous monitoring.

The infrared transmitting substrate 26 alone may be heated by the heating device 38. However, considering that the chemicals adsorbed to the inside surface of the substrate sealing vessel 36 may affect the measurements that follow, preferably both the infrared transmitting substrate 26 and the substrate sealing vessel 36 are heated.

The infrared transmitting substrate 26 alone may be heated by the heating device 38. However, considering that chemicals adsorbed to the inside surface of the substrate sealing vessel 36 may affect the following measurements, preferably both the infrared transmitting substrate 26 and the substrate sealing vessel 36 are heated.

(f) Incidence Optical System 42 (Infrared Light Source 44, Reflection Mirror 48 and Concave Mirror 46)

The infrared light source 44 can be a light source which emits infrared light of a 2-25 µm band corresponding to molecular vibrations of organic molecules. For example, heat rays emitted by applying current to silicon carbide (SiC) or nichrome wires as a filament may be used as the light source. Light sources using SiC, such as SiC globe lanterns, etc., are characterized in that they emit infrared light of a 1.1-25 µm-band and is not burnt even in naked uses in the air.

The reflection mirror 48 and the concave mirror 46 lead the infrared light emitted by the infrared light source 44 into the infrared transmitting substrate at the end surface so that the infrared light make multiple reflections in the infrared transmitting substrate 26.

Setting of the incidence angle of the infrared light is detailed in the specification of Japanese Patent Application No. Hei 11-95853 (1999) filed by the applicant of the present application.

(g) Detection Optical System 52 (Concave Mirror 56 and Reflection Mirror 54) and Infrared Light Detector 50

The concave mirror 56 and the reflection mirror 54 lead the infrared light which has made multiple reflections in the infrared transmitting substrate 26 and exited the end surface of the infrared transmitting substrate 26 to the infrared light detector 50.

The infrared light detector 50 can be an FTIR apparatus incorporating, e.g., an infrared detector of nitrogen cooling InSb or others. The infrared light detector 50 detects via the detection optical system 52 the infrared light exiting the end surface of the infrared transmitting substrate 26 and subjects the infrared light to Fourier-transform spectroscopy.

The FTIR apparatus used as the infrared light detector 50 spectroscopically analyzes the infrared light by the mechanism of Fourier transform spectroscopy based on a double beam interferometer (Michelson interferometer). In place of the FTIR apparatus, an infrared spectrometer using a diffraction grating may be used.

(h) Computer/Display

Monitored data of spectra given by the infrared light detector 50 are supplied to the computer/display 20, where chemicals present in a gas-to-be-monitored are identified, and amounts of the chemicals are computed.

Kinds and calibration curves of chemicals present in a gas-to-be-monitored are separately stored as data base in the memory of the computer/display 20, and with reference to the data base, the monitored data are determined.

For identifying chemicals in gases-to-be-monitored, wave numbers of the infrared absorption of the respective kinds of molecular vibrations of various substances are stored as data base in the computer/display 20. For example, data of absorption wave numbers of respective chemicals, which are caused by $CH_3$ symmetric stretching vibrations, $CH_3$ asymmetric stretching vibrations, $CH_2$ symmetric stretching vibrations, $CH_2$ asymmetric stretching vibrations, etc. are stored in the computer/display 20. When identifying a chemical, out of the data base of the absorption wave numbers of the various molecular vibrations, reference is also made to the data of absorption wave numbers caused by a specific molecular vibration.

The respective constituent elements of the chemical detecting apparatus according to the present embodiment have been detailed above. The sampling pump 40 and the FTIR apparatus 58 have been recently increasingly downsized and thus become more portable. Other constituent elements, e.g., the cooling device 30 using the Peltier device, the heating device 38 in the form of an electric heater, etc. are available in smaller sizes. This makes the chemical detecting apparatus as a whole compact and very portable, which facilitates carrying the device to a site where chemicals must be detected and monitoring the chemicals at the site.

[2] The Chemical Detecting Method

Next, the chemical detecting method according to the present embodiment will be explained with reference to FIG. 9 and FIGS. 11 to 13.

First, the chemical detecting apparatus according to the present embodiment is placed in an environment to be monitored, and the infrared transmitting substrate 26 starts to be cooled by the cooling device 30.

After the infrared transmitting substrate 26 has been sufficiently cooled, the sampling pump 40 is actuated to establish the negative pressure in the substrate sealing vessel 36 to introduce the gas-to-be-monitored into the substrate sealing vessel 36 through the inlet port 32 and flow in the substrate sealing vessel 36. Here, the chemicals in the gas-to-be-monitored can be adsorbed more effectively in larger amounts to the infrared transmitting substrate 26 which is cooled than that adsorbed to the infrared transmitting substrate which is not cooled.

After a period of time necessary for chemicals in the gas-to-be-monitored to be adsorbed to the surface of the infrared transmitting substrate 26 has passed, infrared light is introduced into the infrared transmitting substrate 26 at the end surface by the incidence optical system 42 so that the infrared light makes multiple reflections in the infrared transmitting substrate 26.

The infrared light introduced into the infrared transmitting substrate 26 propagates, making multiple reflections in the infrared transmitting substrate 26.

Subsequently, the infrared light which has made multiple reflections in the infrared transmitting substrate 26 and exited the infrared transmitting substrate 26 at the end surface is detected by the infrared light detector 50 via the detection optical system 52 to give infrared transmission spectra.

Then, based on monitored results given as described above, chemicals present in the gas-to-be-monitored are analyzed. The analysis will be explained by means of an example that acetone, which is a volatile organic chemical, is mixed in the gas-to-be-monitored.

The following should be taken into consideration for analyzing chemicals adsorbed to the surface of the infrared transmitting substrate 26 when implementing the chemical detecting method according to the present embodiment. Infrared transmitting substances, such as ZnSe, GaAs, Ge, etc., which can form the infrared transmitting substrate 26 are not perfectly transparent in all the wave number ranges of infrared light but have absorbance spectra which are intrinsic to their crystals. For example, FIG. 11 shows a graph of the infrared transmission spectrum of GaAs. The infrared transmittances are taken on the vertical axis, and it is shown that as the transmittance is higher, the transparency is higher. As evident in FIG. 11, the infrared transmittance of GaAs greatly varies depending on the wave number ranges of infrared light.

On the other hand, the infrared spectrum of acetone standard sample alone which is a substance to be detected is as shown in FIG. 12.

Accordingly, the infrared spectrum of the acetone adsorbed to the surface of the GaAs substrate is a product of the spectrum of the GaAs substrate shown in FIG. 11 and the spectrum of the acetone standard sample shown in FIG. 12, and is much deformed from the spectrum of acetone alone. Accordingly, even by the direct analysis of the spectrum of the infrared light which has made multiple reflections in the infrared transmitting substrate 26 and exited the infrared transmitting substrate 26, chemicals adsorbed to the surface of the infrared transmitting substrate 26 cannot be identified.

Then, an infrared transmission spectrum of the infrared transmitting substrate 26 whose surface is clean without chemicals adsorbed to is prepared in advance as a reference data.

Next, infrared transmission spectra of the infrared transmitting substrate 26 with chemicals adsorbed to are prepared as monitored data. Then, ratio spectra of the monitored data of the infrared transmitting substrate 26 with chemicals adsorbed to are computed with respect to the reference data. Thus, spectrum components intrinsic to the infrared transmitting substrate 26 are cancelled, and infrared absorbance spectra of the chemicals alone adsorbed to the surface of the infrared transmitting substrate 26 can be obtained.

FIG. 13 shows a spectrum as the monitored result of a gas-to-be-monitored containing acetone by the above-described method. The spectrum of FIG. 13, in which absorbance is taken on the vertical axis, is inverted with respect to the spectrum of the acetone standard sample shown in FIG. 12. However, in the spectrum as the monitored result shown in FIG. 13 convex peaks are detected on the top corresponding to the peaks in the spectrum of the acetone standard sample shown in FIG. 12. This indicates that the above-described method can identify chemicals in a gas-to-be-monitored, based on infrared absorbance spectra of the chemicals adsorbed to the surface of the infrared transmitting substrate 26.

Thus, kinds of chemicals in a gas-to-be-monitored can be identified, based on infrared absorbance spectra of the chemicals adsorbed to the surface of the infrared transmitting substrate 26.

Quantities of the thus identified chemicals can be determined as follows. In advance, intensities of absorption peaks of an ideal gas whose concentration of a chemical is to be detected are monitored by the above-described method, and a calibration curve is prepared as data base. Intensities of absorption peaks of the chemical in a the gas-to-be-monitored actually obtained are compared with the data base to compute a concentration of the chemical in the gas-to-be-monitored.

Next, the infrared transmitting substrate 26 and the substrate sealing vessel 36 are heated by the heating device 38 as required to remove the chemicals adsorbed to the surface of the infrared transmitting substrate 26 and the inside surface of the substrate sealing vessel 36. Thus, fresh monitoring can be performed with the cleaned surfaces of the infrared transmitting substrate 26 and the substrate sealing vessel 36. The cleaning of the infrared transmitting substrate 26 and the substrate sealing vessel 36 by the heating may be performed before fresh monitoring. As described above, the chemical detecting apparatus according to the present embodiment has the mechanism of cleaning the infrared transmitting substrate 26 and the substrate sealing vessel 36, whereby the detection of chemicals can be repeated.

Next, the above-described measurement is repeated as required to thereby measure transient changes, etc. of chemicals in a gas-to-be-monitored.

As described above, according to the present embodiment, while a gas-to-be-monitored is being caused to flow in the substrate sealing vessel 36, chemicals in the gas-to-be-monitored are adsorbed to the surface of the cooled infrared transmitting substrate 26, and the chemicals adsorbed to the surface of the infrared transmitting substrate 26 are monitored by multiple internal reflection FTIR method, whereby the chemicals in the gas-to-be-monitored can be detected with high sensitivity and real time.

Figure 14:
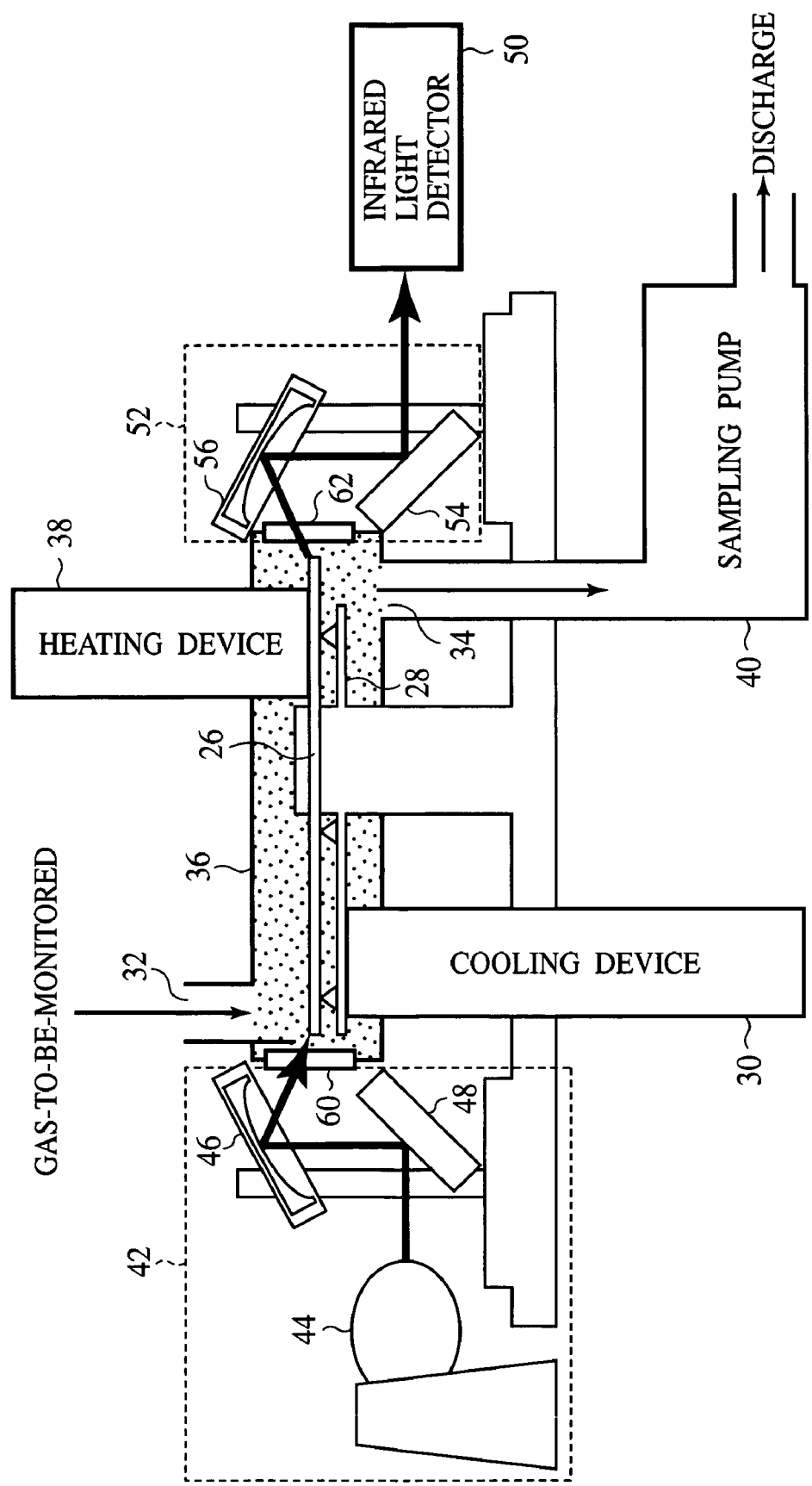
FIG. 14 is a sectional view of the chemical detecting apparatus according to a modification of the first embodiment of the present invention, which shows a structure thereof.

In the present embodiment, both end surfaces of the infrared transmitting substrate 26 are exposed through the side surfaces of the substrate sealing vessel 36. Infrared light is incident on one of the exposed end surfaces, and the infrared light exiting the other exposed end surface is detected. However, as shown in FIG. 14, the whole infrared transmitting substrate may be housed within the substrate sealing vessel 36. In this case, an incidence window 60 and a detection window 62 of an infrared transmitting material are formed in the side surfaces of the substrate sealing vessel 36. The infrared light is incident on one end surface of the infrared transmitting substrate through the incidence window 60, and the infrared light exiting the other end surface is detected by the detection optical system 52 through the detection window 62. The present embodiment, in which both end surfaces of the infrared transmitting substrate 26 are exposed outside through both side surfaces, requires precision machining to ensure the gas tightness of the substrate sealing vessel 36. However, the structure shown in FIG. 14 facilitates higher gas tightness of the substrate sealing vessel 36.

SECOND EMBODIMENT

Figure 15:
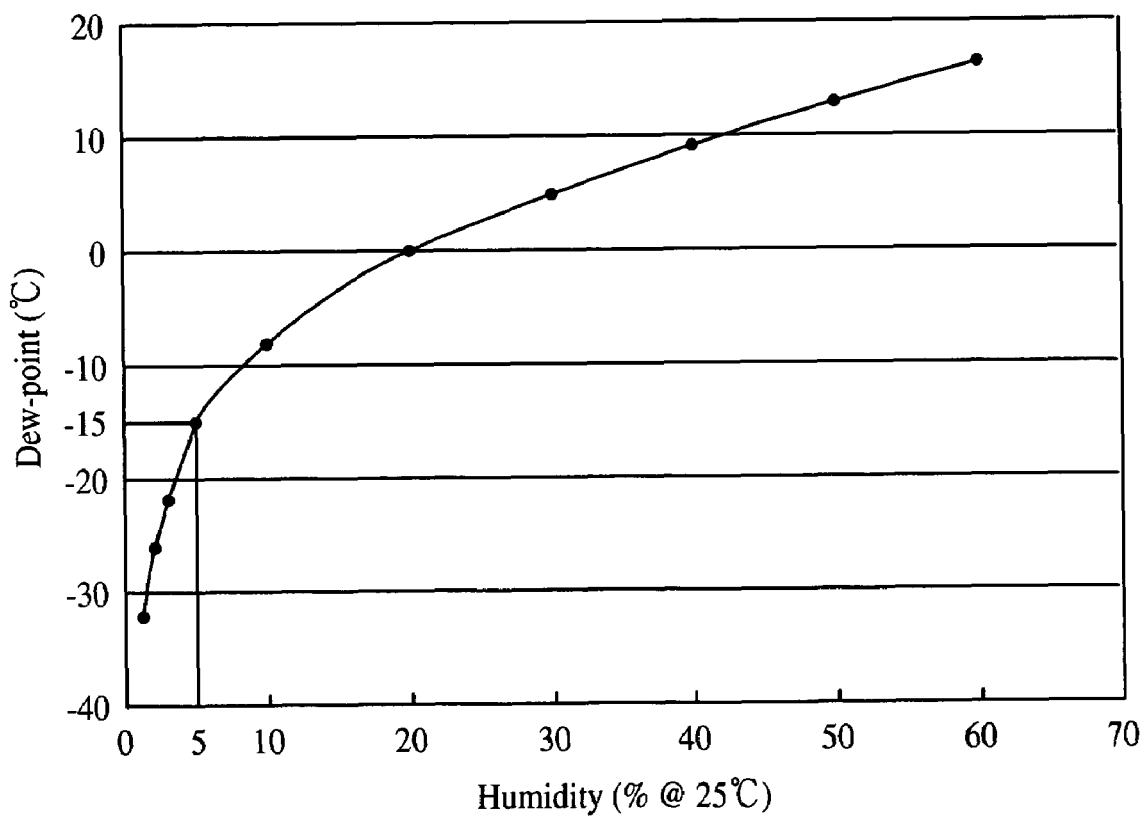
FIG. 15 is a graph of relationships between humidities and dew points at a room temperature of 25° C.
Figure 16:
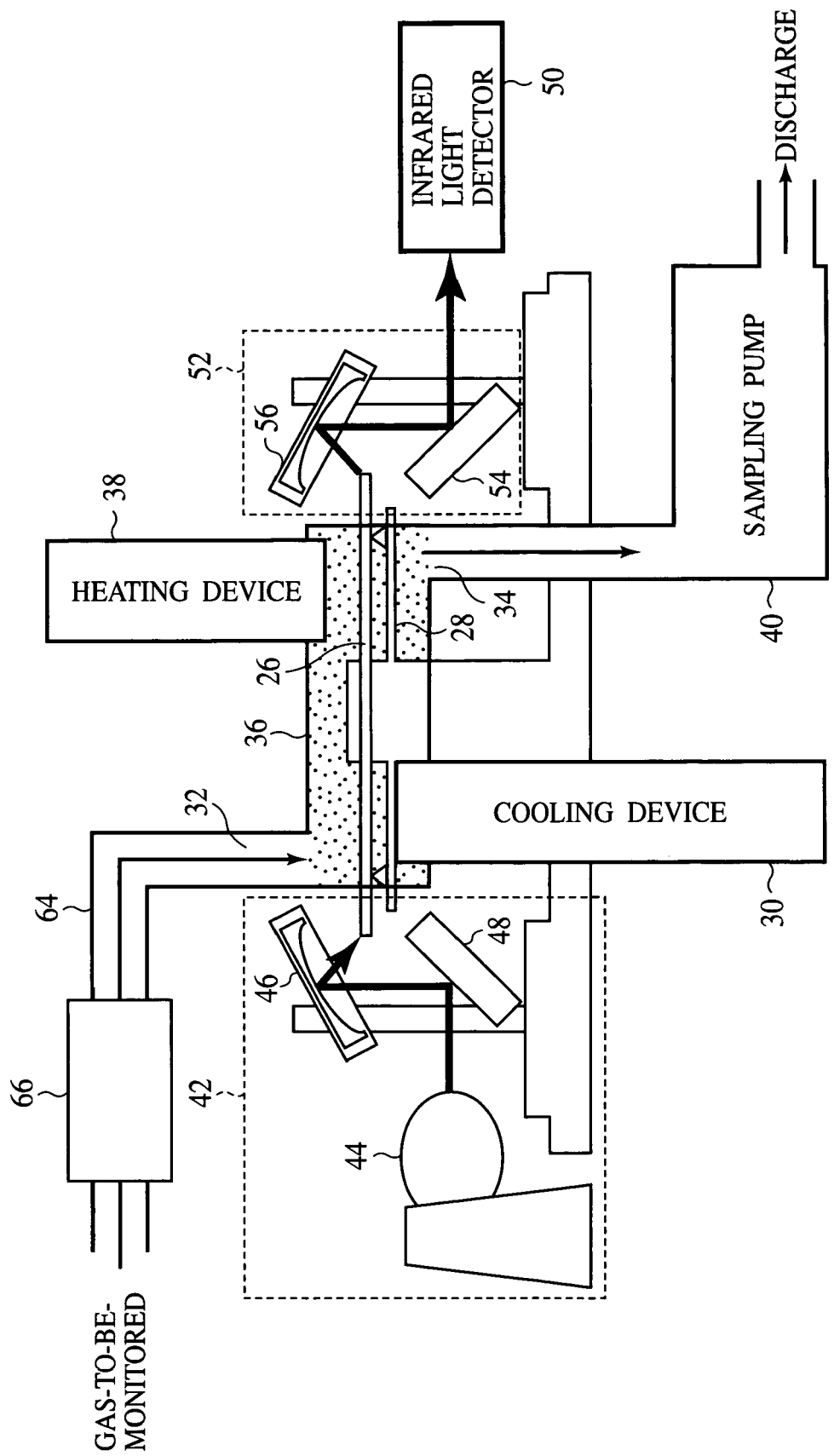
FIG. 16 is a sectional view of the chemical detecting apparatus according to a second embodiment of the present invention wherein the humidity of a gas-to-be-monitored is decreased by a desiccating filter, which shows a structure thereof.
Figure 17:
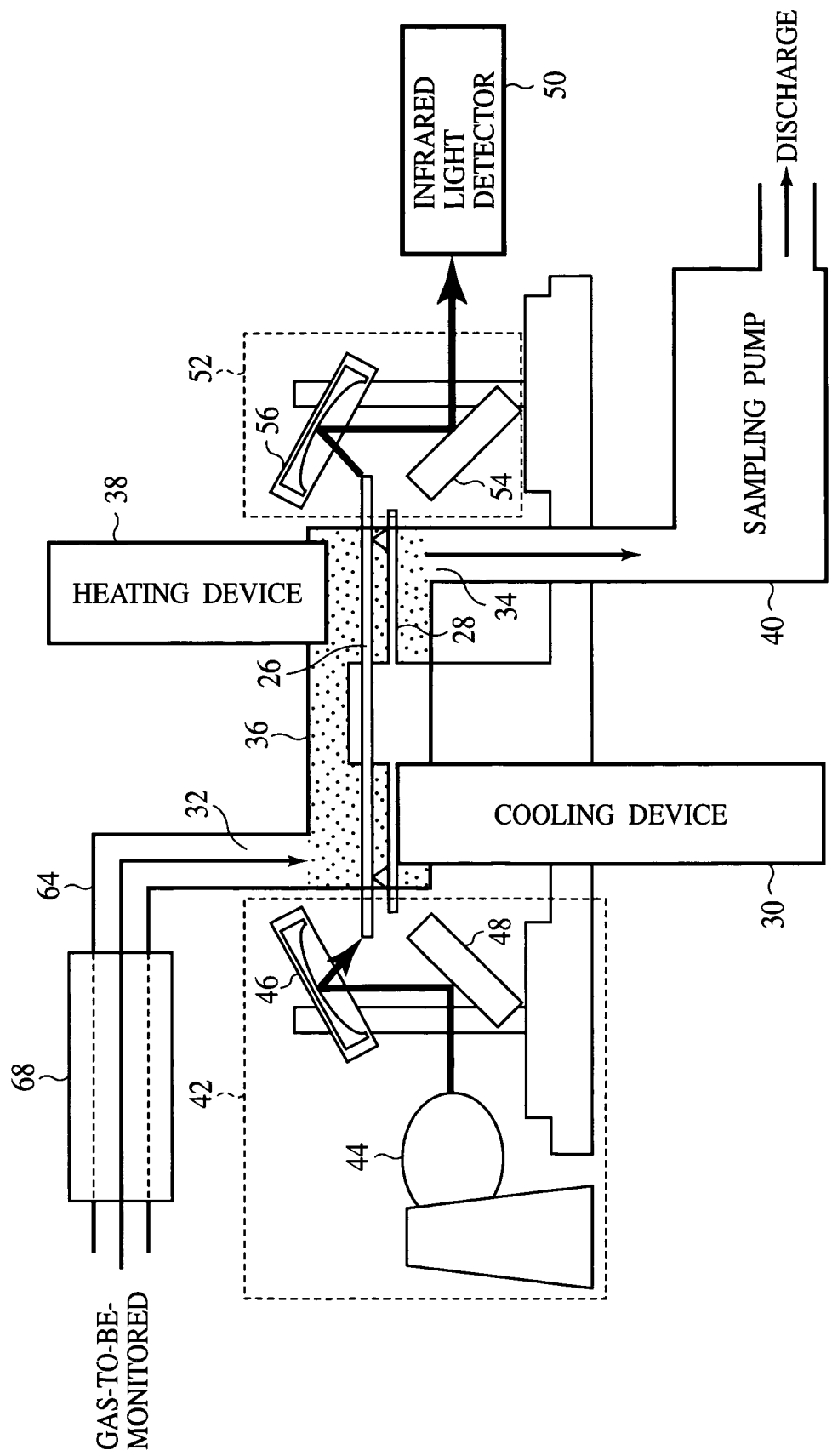
FIG. 17 is a sectional view of the chemical detecting apparatus according to a second embodiment of the present invention wherein the humidity of a gas-to-be-monitored is decreased by a pipe cooling device, which shows a structure thereof.
Figure 18:
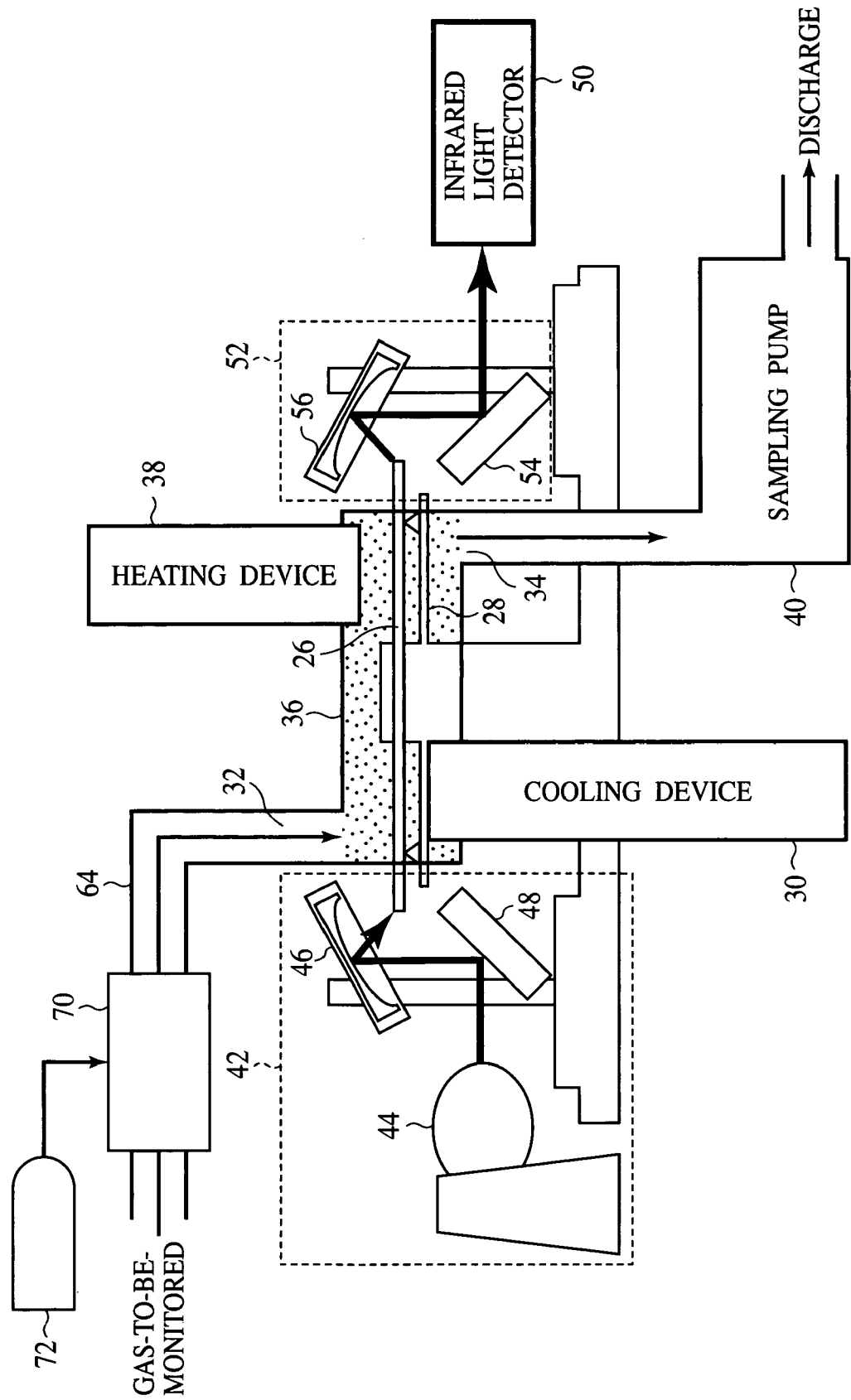
FIG. 18 is a sectional view of the chemical detecting apparatus according to a second embodiment of the present invention wherein the humidity of a gas-to-be-monitored is decreased by a gas mixing device, which shows a structure thereof.
Figure 19:
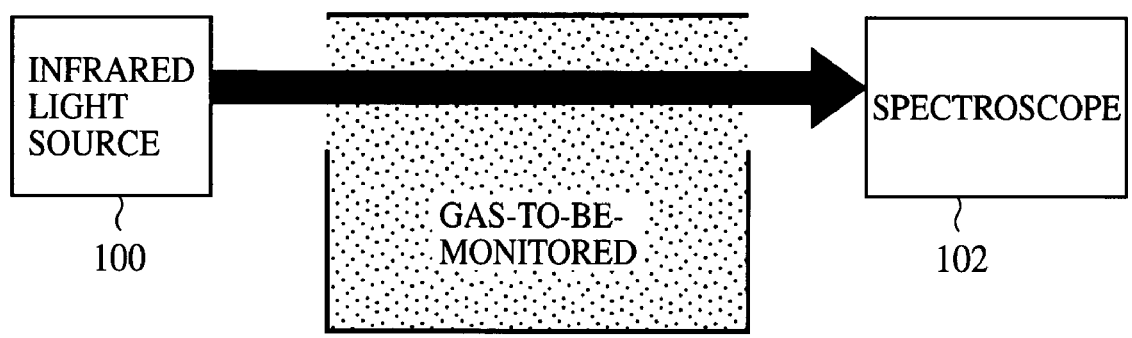
FIG. 19 is a diagrammatic view explaining the measuring principle of FTIR.

The chemical detecting method and apparatus according to a second embodiment of the present invention will be explained with reference to FIGS. 15 to 18. FIG. 15 is a graph of relationships between humidities and dew points at a 25° C. room temperature. FIG. 15 is a sectional view of the chemical detecting apparatus according to the present embodiment, which shows a structure of removing the humidity of a gas-to-be-monitored by a desiccating filter. FIG. 17 is a sectional view of the chemical detecting apparatus according to the present embodiment which shows a structure of decreasing the humidity of a gas-to-be-monitored by a pipe cooling device. FIG. 18 is a sectional view of the chemical detecting apparatus according to the present embodiment which shows a structure of decreasing the humidity of a gas-to-be-monitored by a gas mixing device.

In the chemical detecting method and apparatus according to the fist embodiment, for higher detection sensitivity, the infrared transmitting substrate 26 is cooled by the cooling device 30, whereby the adsorption rate of chemicals to the infrared transmitting substrate 26 is increased. However, in this case there is a risk that the infrared transmitting substrate 26 may dew depending on monitoring conditions, such as the humidity, etc., of the a gas-to-be-monitored.

FIG. 15 is a graph of relationships between humidities and dew points at a room temperature of 25° C. The dew point here means a temperature of the infrared transmitting substrate 26 where dewing starts. For example, the graph shows that the dewing starts at a temperature of the infrared transmitting substrate 26 which is below 12° C. when the humidity is 50% at a 25° C. room temperature.

When water drops are formed on the surface of the infrared transmitting substrate 26 by the dewing, the infrared light making multiple reflections in the infrared transmitting substrate 26 exits the infrared transmitting substrate 26 outside at places where the water drops are adsorbed. Resultantly, the infrared light does not exit at the end surface of the infrared transmitting substrate 26, near which the detection optical system 52 is positioned, and the infrared light fails to arrive at the infrared light detector 50. That is, there is a risk that the dewing of the infrared detecting substrate 26 might make the chemical detection itself impossible.

Accordingly, in the first embodiment, when the infrared transmitting substrate 26 is cooled to increase the adsorption rate of chemicals, the infrared transmitting substrate 26 must be cooled in a temperature range in which the dewing does not take place. For example, at a 25° C. room temperature and a 50% humidity, the temperature difference between the infrared transmitting substrate 26 and the room temperature must be less than 13° C. However, such temperature difference is often insufficient to effectively increase the adsorption rate of chemicals to the infrared transmitting substrate 26.

As described above, in the first embodiment, because the infrared transmitting substrate 26 dews depending on monitoring conditions, the cooling temperature of the infrared transmitting substrate 26 is restricted.

Then, the chemical detecting method and apparatus according to the present embodiment decrease the humidity of a gas-to-be-monitored before fed into the substrate sealing vessel 36 to thereby prevent the infrared transmitting substrate 26 form dewing and to further cool the infrared transmitting substrate 26 to a lower temperature. Thus, the adsorption efficiency of chemicals to the surface of the infrared transmitting substrate 26 can be further improved, and the chemical detection sensitivity can be further improved.

As means for decreasing the humidity of a gas-to-be-monitored before fed into the substrate sealing vessel 36, the following three structures are exemplified.

A first constitution removes water in a gas-to-be-monitored by using a desiccating agent. As shown in FIG. 16, a pipe 64 is connected to the inlet port 32 of the chemical detecting apparatus according to the first embodiment. A desiccating filter 66 filled with a desiccating agent is disposed in the pipe 64. The desiccating agent filled in the desiccating filter 66 is silca gel or others.

A gas-to-be-monitored is fed into the substrate sealing vessel 36 through the desiccating filter 66. That is, water in the gas-to-be-monitored is removed by the desiccating filter 66, and the humidity of the gas-to-be-monitored is decreased. The gas-to-be-monitored having the humidity decreased is exposed to the infrared transmitting substrate 26. Resultantly, the infrared transmitting substrate 26 can be cooled to a lower temperature without dewing the infrared transmitting substrate 26.

For example, when a room temperature is 25° C., a humidity of the gas-to-be-monitored is 50%, a humidity is decreased to 25% by the desiccating filter 66. Then, the infrared transmitting substrate 26 can be cooed to 0° C. without the dewing. On the other hand, when the desiccating filter 66 is not used, the dewing takes place, which hinders the cooling of the infrared transmitting substrate 26 down to only about 12° C.

As described above, a gas-to-be-monitored is desicated by the desiccating filter 66, whereby the infrared transmitting substrate 26 can be cooled to a lower temperature without the dewing. Thus, the adsorption rate of the infrared transmitting substrate of chemical in a gas-to-be-monitored can be increased, and the chemicals in the gas-to-be-monitored can be detected with higher sensitivity.

The above-described desiccating filter 66 using the desiccating agent can decrease the humidity of a gas-to-be-monitored to below about 10% by the very simple and small-sized device constitution.

A second constitution for decreasing in advance the humidity of a gas-to-be-monitored removes water in the gas-to-be-monitored by utilizing dewing. In this case, as shown in FIG. 17, a pipe cooling device 68 for cooling the pipe 64 connected to the inlet port 32 is provided. A gas-to-be-monitored is fed into the substrate sealing vessel 36 while the pipe 64 is being cooled, whereby the inside wall of the pipe 64 is cooled by the pipe cooling device 68 and dews. Thus, the water in the gas-to-be-monitored is removed before fed to the substrate sealing vessel 36. Resultantly, the humidity of the gas-to-be-monitored is decreased, and the infrared transmitting substrate 26 can be cooled to lower the temperature.

A third constitution for decreasing in advance the humidity of a gas-to-be-monitored mixes a desiccating gas, such as dry air, dry nitrogen or others, with the gas-to-be-monitored. In this case, as shown in FIG. 18, a gas mixing device 70 for mixing a gas-to-be-monitored with desiccating gas is disposed in the pipe 64 connected to the inlet port 32. The gas mixing device 70 is connected to a gas cylinder 72 loaded with a desiccating gas to be mixed with a gas-to-be-monitored. The desiccating gas to be mixed with a gas-to-be-monitored preferably contains no special chemical and exhibits infrared absorption as little as possible.

A gas-to-be-monitored is mixed with the desiccating gas in the gas cylinder 72 by the gas mixing device 70 and then fed into the substrate sealing vessel 36. This method has an advantage that the humidity of a gas-to-be-monitored can be decreased without changing an absolute amount ratio of respective chemicals present in a gas-to-be-monitored.

The mixing of the desiccating gas decreases the concentrations of chemicals in a gas-to-be-monitored to be fed into the substrate sealing vessel 36. However, the infrared transmitting substrate 26 can be cooled to lower than in the case that the desiccating gas is not mixed, and the detection sensitivity of chemicals can be increased as a whole.

For example, a gas-to-be-monitored at a 25° C. room temperature and a 50% humidity is fed into the substrate sealing vessel 36 while being mixed at 1:1 with a gas of a 0% humidity by the gas mixing device 70. Thus, the relative humidity of the gas-to-be-monitored can be decreased to 25%, and the infrared transmitting substrate 26 can be cooled to a lower temperature than when the gas-to-be-monitored has a 50% humidity. In this case, a gas-to-be-monitored and the desiccating gas are mixed with each other, whereby concentrations of chemicals to be detected are decreased to 1/2. Accordingly, when a cooled temperature of the infrared transmitting substrate 26 is the same, the detection sensitivity of the chemicals becomes relatively 1/2. However, when the infrared transmitting substrate 26 is further cooled to a lower temperature, whereby the relative sensitivity becomes 10 times, the improvement of the detection sensitivity by 5 times can be realized even when the concentrations of the chemicals become 1/2.

As described above, the means for decreasing in advance the humidity of a gas-to-be-monitored to be fed into the substrate sealing vessel 36 is disposed in the chemical detecting apparatus according to the second embodiment, whereby the infrared transmitting substrate 26 is cooled to a lower temperature. Thus, the adsorption rate of chemicals to the infrared transmitting substrate 26 can be further improved, and the detection sensitivity can be further improved.

In determining a concentration of a chemical in a gas-to-be-monitored in the present embodiment, as in the first embodiment, intensities of absorption peaks of an ideal gas of a chemical whose concentration is known are monitored, and the calibration curve must be prepared. To measure absorption peaks of an ideal gas and prepare the calibration curve, the following two methods are used.

In a first method, an ideal gas is monitored by the above-described method in which the humidity is not decreased in advance to prepare a calibration curve. The ideal gas the concentration of a chemical of which is known is desiccated in advance and does not cause dews. The cooled temperature of the infrared transmitting substrate 26 is equal to that of the gas-to-be-monitored at the time of measurement. Based on the monitored results of the ideal gas, the calibration curve is prepared. By using the calibration curve, based on the monitored result of the gas-to-be-monitored by the method in which the humidity is decreased, the concentration of the chemical in the gas-to-be-monitored is determined.

However, when the gas-to-be-monitored passes through the desiccating filter 66 shown in FIG. 16, there is a possibility that chemicals in the gas-to-be-monitored in addition to the water may be also adsorbed by the desiccating agent. Then, in this case, adsorption coefficients which are ratios of chemicals-to-be-monitored to be adsorbed by the desiccating agent are computed in advance. Concentrations of chemicals computed based on the calibration curve obtained by the first method are corrected by the adsorption coefficients. Thus, concentrations of the chemicals in the gas-to-be-monitored before passing through the desiccating filter are estimated.

Similarly in the desiccation by the pipe cooling device 68 shown in FIG. 17, there is a risk that chemicals in a gas-to-be-monitored may be adsorbed to the inside wall of the cooled pipe 64. Then, in this case as well, ratios of chemicals to be adsorbed to the inside wall of the cooled pipe 64 are given in advance as correction constants. By using the correction constants, concentrations of chemicals computed based on the calibration curve given by the first method are corrected. Thus, concentrations of the chemicals of the gas-to-be-monitored before passing through the cooled pipe 64 are estimated.

Furthermore, in mixing the desiccating gas by the gas mixing device 70 shown FIG. 18, chemicals in a gas-to-be-monitored fed into the gas sealing vessel 36 are diluted. Accordingly, in consideration of dilution rates of concentration due to the mixture with the desiccating gas, concentrations of the chemicals computed based on the calibration curve of the first method are corrected. Thus, concentrations of the chemicals of the gas-to-be-monitored before mixed with the desiccating gas by the gas mixing device 70 are estimated.

As a second method for preparing the calibration curve, by using the above-described means for decreasing the humidity, an ideal gas is monitored under the same conditions for measuring a gas-to-be-monitored to hereby prepare the calibration curve.

For example, in monitoring a gas-to-be-monitored using the desiccating filter 66, the ideal gas is monitored by using the desiccating filter 66 to prepare the calibration curve. The thus-given calibration curve includes amounts of chemicals adsorbed on the desiccating agent of the desiccating filter 66.

Similarly in using the pipe cooling device 68, the calibration curve including amounts of chemicals adsorbed to the cooled pipe 64 can be prepared. In using the gas mixing device 70 as well, the calibration curve including diluted concentrations of chemicals due to the mixture with the desiccating gas can be given.

Accordingly, based on the calibration curve of the second method, concentrations of chemicals in a gas-to-be-monitored before the humidity is decreased can be directly determined without the correction.

As described above, according to the present embodiment, the infrared transmitting substrate 26 is exposed to a gas-to-be-monitored having the humidity decreased in advance, whereby the infrared transmitting substrate 26 can be cooled to lower temperatures without the dewing. However, the efficiency of chemicals in a gas-to-be-monitored to be adsorbed to the surface of the infrared transmitting substrate 26 can be further improved. Thus, the detection sensitivity of detecting chemicals in a gas-to-be-monitored can be further improved.

MODIFIED EMBODIMENTS

The present invention is not limited to the above-described embodiments and includes other various modifications.

For example, in the above-described embodiments, the infrared transmitting substrate 26 is heated by the heating device 38 to purify the surface of the infrared transmitting substrate 26, but the purifying method for purifying the surface is not limited to the method described above. For example, an ultraviolet radiation emitting apparatus for emitting ultraviolet radiation to the infrared transmitting substrate 26 may be provided. The ultraviolet radiation is applied to the infrared transmitting substrate 26, and oxidizing ability of ozone generated when the ultraviolet radiation is emitted into the atmosphere and the energy of the ultraviolet radiation itself are used to decompose and remove the chemicals adsorbed to the surface of the infrared transmitting substrate 26. The effect of purifying chemicals by the application of ultraviolet radiation is detailed in, e.g., Kohji Honma, "UV Ozone Seimitsusenjou (UV Ozone Precision Cleaning)" (Nippon Eisei Shigaisen Kenkyukai-shi, vol. 9, No. 2, October 1990).

In the above-described embodiments, the surface of the infrared transmitting substrate 26 is purified by the heating device 38. However, depending on a required monitoring precision, etc., the means for purifying the surface of the infrared transmitting substrate 26 may not be essential. The infrared transmitting substrate 26 may be replaced with another infrared transmitting substrate 26 having the surface purified suitably based on monitoring times or others.

In the above-described embodiments, the infrared transmitting substrate 26 is housed in the substrate sealing vessel 36, and a gas-to-be-monitored is caused to flow by the sampling pump 40. However, the infrared transmitting substrate 26 may not necessarily be housed in the substrate sealing vessel 36 but is exposed directly to the gas-to-be-monitored. In this case, the cooling device 30 enhances the adsorption of chemicals in a gas-to-be-monitored. It is possible that gas flowing means, such as an electric fan or the like, for flowing a the gas-to-be-monitored with respect to the infrared transmitting substrate 26 is provided to enhance the adsorption of chemicals in the gas-to-be-monitored to the infrared transmitting substrate 26.

In the above-described embodiments, chemicals adsorbed to the surface of the infrared transmitting substrate 26 are monitored by multiple internal reflection FTIR method, but the method for detecting chemicals adsorbed to the surface is not limited to the methods described above.

The chemical detecting method and apparatus according to the present invention are useful to identify generation sources of chemicals, control and administer discharge amounts of chemicals to environments and detect various chemicals present in environments at high speed and with high sensitivity.

The invention claimed is:

1. A chemical detecting method, comprising:

exposing a substrate for a chemical to be adsorbed thereto, to gas-to-be-monitored;

enhancing the adsorption of the chemical contained in the gas-to-be-monitored to the substrate;

applying an infrared light to the substrate with the chemical adsorbed thereto;

analyzing the infrared light which has passed through and exited the substrate or has been reflected on the surface of the substrate to thereby identify a kind of the chemical adsorbed to the substrate and/or compute an adsorption amount of the chemical; and identifying a kind of the chemical in the gas-to-be-monitored and/or computing a concentration of the chemical, based on the amount of the chemical adsorbed to the substrate;

wherein the substrate is cooled to thereby enhance the adsorption of the chemical in the gas-to-be-monitored to the substrate; and wherein the substrate is exposed to the gas-to-be-monitored after a relative humidity of the gas-to-be-monitored has been decreased.

2. A chemical detecting method according to claim 1, wherein
the gas-to-be-monitored is desiccated to decrease a relative humidity of the gas-to-be-monitored.

3. A chemical detecting method according to claim 1, wherein
the gas-to-be-monitored is mixed with a desiccating gas to decrease a relative humidity of the gas-to-be-monitored.

4. A chemical detecting method according to claim 1, wherein
a concentration of the chemical in the gas-to-be-monitored is computed in consideration of a concentration of the chemical which has been decreased corresponding to the decrease of the relative humidity of the gas-to-be-monitored.

5. A chemical detecting method according to claim 1, wherein
the gas-to-be-monitored is flowed with respect to the surface of the substrate to enhance the adsorption of the chemical in the gas-to-be-monitored to the substrate.

6. A chemical detecting method according to claim 5, wherein
the substrate is housed in a vessel having an inlet port and an outlet port, and the gas-to-be-monitored is fed into the vessel through the inlet port and discharged through the outlet port to thereby flow the gas-to-be-monitored.

7. A chemical detecting method according to claim 1, wherein
the substrate is formed of a substance which transmits the infrared light; and
the infrared light which has made multiple reflections in the substrate and exited the substrate is analyzed to identify a kind of the chemical adsorbed to the substrate and/or compute an adsorption amount of the chemical.

8. A chemical detecting method according to claim 1, wherein
the substrate is formed of a substance which transmits the infrared light; and
the infrared light which has been incident on one surface of the substrate and exited the substrate at the other surface is analyzed to thereby identify a kind of the chemical adsorbed to the substrate and/or compute an adsorption amount of the chemical.

9. A chemical detecting method according to claim 1, wherein
the substrate comprises a pair of substrates which are arranged substantially in parallel with each other; and
the infrared light which has made multiple reflections between the pair of substrates and exited the substrate to thereby identify a kind of the chemical adsorbed to the substrate and/or compute an adsorption amount of the chemical.

10. A chemical detecting method according to claim 1, wherein
the chemical adsorbed to the substrate is periodically removed to initialize a surface state of the substrate.

11. A chemical detecting method according to claim 10, wherein
the substrate is heated to remove the chemical adsorbed to the substrate.

12. A chemical detecting method according to claim 10, wherein
an ultraviolet radiation is applied to the substrate to remove the chemical adsorbed to the substrate.

13. A chemical detecting apparatus comprising:
a substrate for a chemical in gas-to-be-monitored to be adsorbed thereto;
an adsorption rate improving means for enhancing the adsorption of the chemical in the gas-to-be-monitored to the substrate, the adsorption rate improving means being a cooling device for cooling the substrate;
an infrared application means for applying an infrared light to the substrate with the chemical adsorbed thereto;
an infrared analyzing means which analyzes the infrared light exiting the substrate after passed through the substrate to thereby identify a kind of the chemical adsorbed to the substrate and/or compute an adsorption amount of the chemical; and
a chemical detecting means which identifies a kind of the chemical in the gas-to-be-monitored and/or compute an adsorption amount of the chemical, based on an analysis result given by the infrared analyzing means;
wherein the cooling device cools a part of the substrate, which is not an optical path of the infrared light.

14. A chemical detecting apparatus according to claim 13, wherein
the substrate is formed of a substance transmitting the infrared light; and
the infrared analyzing means analyzes the infrared light which has made multiple reflections in the substrate and exited the substrate to thereby identify a kind of the chemical adsorbed to the substrate and/or compute an adsorption amount of the chemical.

15. A chemical detecting apparatus according to claim 13, wherein
the substrate is formed of a substance which transmits the infrared light; and
the infrared analyzing means analyzes the infrared light which has been incident on one surface of the substrate, passed through the substrate and exited the other surface of the substrate to thereby identify a kind of the chemical adsorbed to the substrate and/or compute an adsorption amount of the chemical.

16. A chemical detecting apparatus according to claim 13, wherein
the substrate comprises a pair of substrates which are arranged substantially in parallel with each other; and
the infrared analyzing means analyzes the infrared light which has made multiple reflections between the pair of substrates and exited the substrate to thereby identify a kind of the chemical adsorbed to the substrate and/or compute an adsorption amount of the chemical.

17. A chemical detecting apparatus according to claim 13, further comprising:
a humidity decreasing means which decreases a relative humidity of the gas-to-be-monitored.

18. A chemical detecting apparatus according to claim 17, wherein
the humidity decreasing means is a filter for desiccating the gas-to-be-monitored.

19. A chemical detecting apparatus according to claim 17, wherein the humidity decreasing means comprises a cooling means which cools the gas-to-be-monitored before arriving at the infrared transmitting substrate, and the inside of the cooling means is dewed to thereby desiccate the gas-to-be-monitored to decrease a relative humidity of the gas-to-be-monitored.

20. A chemical detecting apparatus according to claim 17, wherein the humidity decreasing means mixes the gas-to-be-monitored with a desiccating gas to thereby decrease a relative humidity of the gas-to-be-monitored.

21. A chemical detecting apparatus according to claim 13, further comprising:

a vessel housing the substrate; and a gas flowing means which makes the gas-to-be-monitored flow in the vessel.

22. A chemical detecting apparatus according to claim 13, further comprising:

a substrate purifying means which removes the chemical adsorbed to the surface of the substrate to initialize a surface state of the substrate.

23. A chemical detecting apparatus according to claim 22, wherein the substrate purifying means heats the substrate to remove the chemical adsorbed to the substrate.

24. A chemical detecting apparatus according to claim 22, wherein the substrate purifying means applies an ultraviolet radiation to the surface of the substrate to remove the chemical adsorbed to the substrate.

* * * * *